(12) United States Patent
Kunkel et al.

(10) Patent No.: US 9,383,299 B2
(45) Date of Patent: Jul. 5, 2016

(54) METHOD FOR HARVESTING NANOPARTICLES AND SEQUESTERING BIOMARKERS

(71) Applicants: Alessandra Luchini Kunkel, Burke, VA (US); Lance Liotta, Bethesda, MD (US); Emanuel Petricoin, Gainsville, VA (US); Barney Bishop, Annandale, VA (US); Francesco Meani, Lugano (CH); Claudia Fredolini, Stockholm (SE); Thomas M Dunlap, Round Hill, VA (US); Alexis Patanarut, Burke, VA (US)

(72) Inventors: Alessandra Luchini Kunkel, Burke, VA (US); Lance Liotta, Bethesda, MD (US); Emanuel Petricoin, Gainsville, VA (US); Barney Bishop, Annandale, VA (US); Francesco Meani, Lugano (CH); Claudia Fredolini, Stockholm (SE); Thomas M Dunlap, Round Hill, VA (US); Alexis Patanarut, Burke, VA (US)

(73) Assignee: GEORGE MASON RESEARCH FOUNDATION, INC., Fairfax, VA (US)

( * ) Notice: Subject to any disclaimer, the term of this patent is extended or adjusted under 35 U.S.C. 154(b) by 365 days.

(21) Appl. No.: 13/776,631

(22) Filed: Feb. 25, 2013

(65) Prior Publication Data

US 2014/0045274 A1   Feb. 13, 2014

Related U.S. Application Data

(63) Continuation of application No. 12/194,371, filed on Aug. 19, 2008, now Pat. No. 8,382,987.

(51) Int. Cl.
| | |
|---|---|
| *B01D 39/16* | (2006.01) |
| *G01N 1/40* | (2006.01) |
| *B01D 15/00* | (2006.01) |
| *B01D 15/02* | (2006.01) |
| *B01D 15/38* | (2006.01) |
| *B01J 20/26* | (2006.01) |
| *B82Y 15/00* | (2011.01) |
| *B01D 15/34* | (2006.01) |

(52) U.S. Cl.
CPC ............ *G01N 1/405* (2013.01); *B01D 15/00* (2013.01); *B01D 15/02* (2013.01); *B01D 15/3804* (2013.01); *B01J 20/26* (2013.01); *B01J 20/261* (2013.01); *B01J 20/264* (2013.01); *B01J 20/265* (2013.01); *B82Y 15/00* (2013.01); *B01D 15/34* (2013.01); *B01D 15/3861* (2013.01); *B01J 2220/54* (2013.01); *Y10T 436/255* (2015.01)

(58) Field of Classification Search
CPC ....................................................... B01D 39/16
See application file for complete search history.

(56) References Cited

PUBLICATIONS

I. Y. Galaev and B. Mattiason, 'Smart' Polymers and What They Could Do in Biotechnology and Medicine, 17 Trends Biotechnol. 335-340 (1999).*
S. Nayak and L. A. Lyon, Ligand-Functionalized Core/Shell Microgels with Permselective Shells, 43 Angew. Chem. Int. Ed. 6706-6709 (2004).*
Abersold et al., Proteome Res 2005, 4, (4), 1104-9.
Srinivas et al., Clin Chem 2002, 48, (8), 1160-9.
Frank and Hargreaves; Nature reviews 2003, 2, (7), 566-80.
Espina et al. Proteomics 2003, 3, (11), 2091-100.
Anderson and Anderson, Mol Cell Proteomics 2002, 1, (11), 845-67.
Lopez et al., Clinical chemistry 2007, 53, (6), 1067-74.
Conrads et al., BioTechniques 2006, 40, (6), 799-805.
Lowenthal et al., Clin Chem 2005, 51, (10), 1933-45.
Lopez et al., Clinical chemistry 2005, 51, (10), 1946-54.
Zolotarjova et al., Proteomics 2005, 5, (13), 3304-13.
Camerini et al., Proteomics Clin. Appl. 2007, 1, 176-184.
Geho et al., Bioconjug Chem 2006, 17, (3), 654-61.
Tirumalai et al., Molecular & cellular proteomics 2003, 2, (10), 1096-103.
Merrell et al., J of biomolecular techniques 2004, 15, (4), 238-48.
Orvisky et al., Proteomics 2006, 6, (9), 2895-902.

* cited by examiner

*Primary Examiner* — Randy Boyer
(74) *Attorney, Agent, or Firm* — Michael L. Greenberg, Esq.; Greenberg & Lieberman, LLC

(57) ABSTRACT

Capture particles for harvesting analytes from solution and methods for using them are described. The capture particles are made up of a polymeric matrix having pore size that allows for the analytes to enter the capture particles. The pore size of the capture particles are changeable upon application of a stimulus to the particles, allowing the pore size of the particles to be changed so that analytes of interest remain sequestered inside the particles. The polymeric matrix of the capture particles are made of co-polymeric materials having a structural monomer and an affinity monomer, the affinity monomer having properties that attract the analyte to the capture particle. The capture particles may be used to isolate and identify analytes present in a mixture. They may also be used to protect analytes which are typically subject to degradation upon harvesting and to concentrate low an analyte in low abundance in a fluid.

1 Claim, 23 Drawing Sheets

METHOD FOR HARVESTING NANOPARTICLES AND SEQUESTERING BIOMARKERS

STATEMENT OF PRIORITY

This application is a continuation of application Ser. No. 12/194,371 filed on Aug. 19, 2008, which was issued as U.S. Pat. No. 8,382,987 on Feb. 26, 2013; which in turn claimed benefit of application No. 60/986,803 filed on Nov. 9, 2007, and was a CIP of application Ser. No. 11/527,727 filed on Sep. 27, 2006, as well as a CIP of application Ser. No. 12/033,701 filed on Feb. 19, 2008.

FIELD OF THE INVENTION

The present invention relates to particles for the harvesting of biomarkers from a mixture as well as methods for using the particles. More specifically, the present invention relates to particles capable of sequestering a biomarker from a mixture, allowing for the separation of the biomarker from the mixture, as well as methods for sequestering biomarkers. More specifically in terms of one application, the present invention provides for the use of harvesting nanoparticles to capture, protect from degradation, and amplify the concentration of low abundance biomarkers in urine.

BACKGROUND OF THE INVENTION

Biomarkers can provide for early stage detection of a wide variety of diseases. As such, there is an urgent need to discover novel biomarkers that provide sensitive and specific disease detection (Aebersold et al., *Proteome Res* 2005, 4, (4), 1104-9; Srinivas et al., *Clin Chem* 2002, 48, (8), 1160-9). Biomarkers provide a way to diagnose a disease before clinical pathologies appear, allowing for early stage treatment of the disease, which typically provides better results.

For example, cancer is rapidly becoming the leading cause of death for many population groups in the United States, largely due to the fact that various types of the disease are usually diagnosed after the cancer has metastasized. At this later stage of the disease, treatment is typically invasive and ineffective. It is widely believed that early detection of cancer prior to metastasis will lead to a dramatic improvement in treatment outcome.

Biomarkers are also continually being discovered that are indicative of various other disease states and conditions as varied as Alzheimer's disease and diabetes. For many of these diseases, the early diagnosis of the disease allows for treatment options that have a greater chance of success than late stage treatment. Further, in some cases, early diagnosis of a disease or predisposition to a disease may even allow the person diagnosed to make lifestyle changes that may help to prevent and reverse the course of the disease without the need for more involved medical treatment.

Biomarkers are nucleic acids, proteins, protein fragments or metabolites indicative of a specific biological state, that are associated with the risk of contraction or presence of disease (Frank and Hargreaves; *Nature reviews* 2003, 2, (7), 566-80). Biomarker research has revealed that low-abundance circulating proteins and peptides present a rich source of information regarding the state of the organism as a whole (Espina et al. *Proteomics* 2003, 3, (11), 2091-100). Two major hurdles have prevented these discoveries from reaching clinical benefit: 1) disease-relevant biomarkers in blood or body fluids may exist in exceedingly low concentrations within a complex mixture of biomolecules and could be masked by high-abundance species such as albumin, and 2) degradation of protein biomarkers can occur immediately following the collection of blood or body fluid as a result of endogenous or exogenous proteinases.

The concentration of proteins and peptides comprising the complex circulatory proteome ranges from 10-12 mg/mL to 10-3 mg/mL, spanning ten orders of magnitude, with a few high molecular weight proteins such as albumin and immunoglobulins accounting for 90% of total protein content (Anderson and Anderson, *Mol Cell Proteomics* 2002, 1, (11), 845-67). However, the low abundance and low molecular weight proteins and metabolites also present in the blood provide a wealth of information and have great promise as a source of new biomarkers. Conventional methods, such as two dimensional gel electrophoresis, do not have the sensitivity and resolution to detect and quantify low abundance low molecular weight proteins and metabolites. Also, in spite of the moderately high sensitivity of modern mass spectrometers (attomolar concentration), their working range spans over three-four orders of magnitude and therefore the less abundant proteins are masked by more abundant proteins. Consequently, the usual sample preparation steps for mass spectrometry (MS) experiments begin with depletion of high abundant proteins using commercially available immunoaffinity depletion columns (Agilent, Sigma, and Beckman-Coulter). After depletion, fractionation is performed by means of size exclusion chromatography, ion exchange chromatography, and/or isoelectric focusing. However, removal of abundant native high molecular weight proteins can significantly reduce the yield of candidate biomarkers because it has been recently shown that the vast majority of low abundance biomarkers are non-covalently and endogenously associated with the carrier proteins that are being removed (Lopez et al., *Clinical chemistry* 2007, 53, (6), 1067-74; Conrads et al., *BioTechniques* 2006, 40, (6), 799-805; Lowenthal et al., *Clin Chem* 2005, 51, (10), 1933-45; Lopez et al., *Clinical chemistry* 2005, 51, (10), 1946-54). Methods, such as size exclusion ultrafiltration under denaturing conditions (Zolotarjova et al., *Proteomics* 2005, 5, (13), 3304-13), continuous elution denaturing electrophoresis (Camerini et al., *Proteomics Clin. Appl.* 2007, 1, 176-184), or fractionation of serum by means of nanoporous substrates (Geho et al., *Bioconjug Chem* 2006, 17, (3), 654-61) have been proposed to solve this problem. Moreover, these same recent findings point to the low molecular weight region of the proteome, as a rich and untapped source of biomarker candidates (Tirumalai et al., *Molecular & cellular proteomics* 2003, 2, (10), 1096-103; Merrell et al., *J of biomolecular techniques* 2004, 15, (4), 238-48; Orvisky et al., *Proteomics* 2006, 6, (9), 2895-902).

In addition to the difficulties associated with the harvest and enrichment of candidate biomarkers from complex natural protein mixtures (such as blood), the stability of these potential biomarkers poses a challenge. Immediately following blood procurement (e.g. by venipuncture) proteins in the serum become susceptible to degradation by endogenous proteases or exogenous environmental proteases, such as proteases associated with the blood clotting process, enzymes shed from blood cells, or associated with bacterial contaminants. Therefore, candidate diagnostic biomarkers in the blood may be subjected to degradation during transportation and storage. This becomes an even more important issue for the fidelity of biomarkers within large repositories of serum and body fluids that are collected from a variety of institutions and locations where samples may be shipped without freezing.

As such, there is a need in the art for particles that allow enrichment and encapsulation of selected classes of proteins and peptides from complex mixtures of biomolecules such as plasma, and protect them from degradation during subsequent sample handling. The captured analytes could then be readily extracted from the particles by electrophoresis allowing for subsequent quantitative analysis. Particles of this type would provide a powerful tool that is uniquely suited for the discovery of novel biomarkers for early stage diseases such as cancer.

Use of harvesting nanoparticles as created in a laboratory by the inventors of the present invention also has been shown to capture, protect from degradation, and amplify the concentration of low abundance biomarkers in the urine. Human growth hormone within urine at low undetectable concentrations was concentrated by particle sequestration to be readily measured by a standard clinical grade immunoassay. For the first time this labile and low abundance biomarker can now be routinely screened in the urine. Physiologic salt and urea concentration does not affect the function of the particle sequestration. The captured biomarker is preserved and stable at room temperature or at 37 C. This finding is applicable to any desired biomarker that can be captured by the particles and uniquely solves a need, particularly in the area of "doping."

GH levels measurement is a key tool, in clinics, for diagnosis of disorders in its secretion, either childhood and adulthood insufficiency or overproduction. In the last few years hGH levels detection has become important as a doping control measure. Despite there being a lack of scientific evidence demonstrating that hGH at superphysiological doses exerts performance enhancing effects, anecdotal evidence suggest its wide abuse (alone or in combination with other anabolic or oxygen transport increasing substances) among bodybuilders and endurance athletes. The measurement of GH in blood or urine is a considerable challenge both because of the hormone biology and technological limitations. The several factors that influence its secretion and the very short half life of hGH lead to high fluctuating levels in the blood and interindividuallintraindividual variability, making hard to define precise cut-off levels to discriminate between physiological raise and what can be from external administration. In particular physical activity itself leads to hGH increase in serum. Depending on time and intensity of exercises, levels can increase by 5-10 folds. Moreover the aminoacid sequence of the recombinant (rhGH) form is identical to the major 22 KDa pituitary isoform, making it impossible to discriminate between the recombinant and the natural isoform. At present two main methods (both using immunologic assays) have been developed to detect GH DOPING using blood samples: the DIRECT and INDIRECT approaches. The direct approach, also known as the "isoform differential immunoassay", exploits the differences in the proportions of hGH isoforms under physiological conditions and following doping practice.

Actually the assumption of rhGH leads to an increase of the 22 KDa isoform and significant decrease of the endogenous pituitary-derived non 22 KDa isoform by negative feedback mechanism. This test was first introduced at the 0 lympic Games in Athens 2004 and Turin 2006. The critical limitation of this assay is the time window of detection, claimed to be between 24 and 36 hours after the last injection, depending on dosage. (3; 2)

The indirect approach ("marker method") is based on measurement of hGH dependent factors that could serve as farmacodynamics markers of its activity (IGF-I, IGFBP-3, Procollagen-III-Terminal Peptide, Osteocalcin, Bone Alkaline Phosphatase and Leptine). (5) Such markers show a longer half life and less variability than GH itself and their measurement could lead, by use of discriminatory mathematical formulas to the identification of rhGH administration. Unfortunately slight but significant changes after acute exercise and interindividual variability make the use of indirect measurement impossible in forensic setting.

Although in the past few years GH measurement techniques have considerably improved in sensitivity, speed, convenience and throughput, still require a full validation. The need for new analytical techniques to fight against doping is far from being fulfilled.

A good anti-doping assay should consider the biological behavior of hGH, be sensitive, with a high degree of accuracy and reproducibility, but also practical and not expensive. Because of its convenient availability and relatively unlimited volume, an anti-doping test on urine samples could be an attractive alternative. Many efforts have been made to detect hGH in urine, both for clinical and anti doping purpose and different immunologic assay have been applied (NordiTest U-hGH assay, Nichols institute Chemoluminescence hGH Immunoassay) (7; 8), but the very low concentration of the hormone in such biologic fluid (between 100 and 1000 time less than in blood—in low nanogram/liter range) and the poor discriminatory capacity of urinary hGH measurement, have so far limited its applications. The present invention offers a novel nanotechnology based on Nanoparticles to concentrate and preserve hGH in Urine so that hGH can be measured with clinical routinely used immunometric assay (IMMULITE-Siemens Medical Solution Diagnostic) for clinical quantitative measurement of hGH in serum.

SUMMARY OF THE INVENTION

It is an object of the present invention to provide capture particles for biomarker harvesting. The capture particles are made up of materials that allow for the sequestering of biomarkers to extract them from mixtures and to protect them from degradation. In one embodiment of the present invention, the capture particles have the ability to specifically capture molecular species having a defined molecular size, mass, and or affinity characteristic and are used to isolate molecules of interest from a sample typically containing a plurality of different molecular species. The capture particles are added to the sample and then utilized to capture the molecular species of interest.

It is a further object of the present invention to provide smart hydrogel particles for biomarker harvesting. The smart hydrogel particles of the present invention may have a porosity and overall size that can be changed by changing the environment surrounding the smart hydrogel particles. The smart hydrogel particles may have a porosity that allows for biomarkers to enter the hydrogel under certain conditions, after which, the conditions surrounding the smart hydrogel particle may change so that the biomarkers are sequestered inside of the smart hydrogel particle.

It is a still further object of the present invention to provide capture particles for biomarker harvesting that have an attractant capable of attracting and interacting with a biomarker. It should be noted that the term attractant is hereinafter synonymous with the term bait and affinity monomer. Also, the term mixture is synonymous with the term solution. In certain embodiments, the attractant will be present inside of the capture particle. In other embodiments, the attractant is part of the material that makes up the capture particle itself.

It is a further object of the present invention to provide capture particles for biomarker harvesting having one or more of the following characteristics: a) an ability to select the size and/or mass of the molecule to be captured, b) an ability to select the affinity properties of the molecule to be captured, and/or c) an ability to capture and/or release the desired molecule in response to a physical or chemical treatment.

It is yet another object of the present invention to provide capture particles for biomarker harvesting that can be easily isolated and separated from mixtures after sequestering of biomarkers is complete. In certain embodiments of the present invention, the capture particles may have characteristics or modifications that allow for them to be separated from mixtures through the application of physical force, electric or magnetic fields, or by the attraction of a moiety on the particle to target.

It is yet another object of the present invention to provide kits for identifying an analyte present in a mixture or solution. The kits of the present invention have some type of collecting device which is typically filled or coated with the capture particles. A solution or other mixture containing the analyte can then be applied to the collecting device, allowing the capture particles to sequester and isolate the desired analyte for analysis.

It is yet another object of the present invention to provide a micro fluidics system for analysis of analytes captured from a solution. The micro fluidic system will have capture particles of the present invention. The sample containing the analyte to be analyzed is introduced into the micro fluidics system, where the capture particles sequester the analyte. The capture particles are then transferred to a separate location where the analyte is released and analyzed using methods known in the art.

The GH is secreted in a pulsatile pattern under hypothalamic control, mediated by the stimulating Gh releasing Hormon (GHRH) and the hinibiting hormone somatostatin (2, 3). Its secretion is influenced by several physiological and pathopysiological conditions such as gender, age, sleep, fever, physical exercise, nutritional state and other metabolic factors. As a result GH levels in blood fluctuate widely. In humans GH levels reach 50-100 ug/l at peak and fall below 0.03 ug/l at nadir. (6) Secretion is slightly higher in women than in men, with the highest levels observed at puberty. Mean levels decrease with age by around 14% per decade.

Blood contains a complex combination of GH multiple isoforms: a major 22-KDa form—the most bioactive—and minor isoforms deriving from alternative m-RNA splicing or proteolitic clivage of the mature protein (20 KDa isoform, modified hGH, acidic hGH, fragmented hGH). hGH also exists in circulating homodimers and heterodimers and approximately 45% of circulating GH is complexed with hGHBPs (GH Binding Proteins). The unbound 22 KDa hGH has a blood half life of 10-20 min, while the proportion bound to hGH-binding proteins has a significantly longer half life (1; 4)

The principal metabolic clearance of GH proceeds through glomerular filtration, reabsorption and degradation in proximal tubular cells. Being such a degradation very efficient, only a very minute amount of filtrated hGH reaches the final urine (<0.01%). (6)

Binding specific membrane receptors ubiquitously expressed, hGH affects protein, fat, carbohydrate and mineral metabolism. It has both direct and indirect effects, the letter being mediated by IGF-I, which is generated in the liver in response to hGH. It enhances anabolism in musculoskeletal system, increasing glucose and aminoacid uptake, while in adipose tissue stimulates lypolisis. In general exerts positive effects on body composition, tissue repairing process and performance.

DETAILED DESCRIPTION OF THE INVENTION

Figure 1:
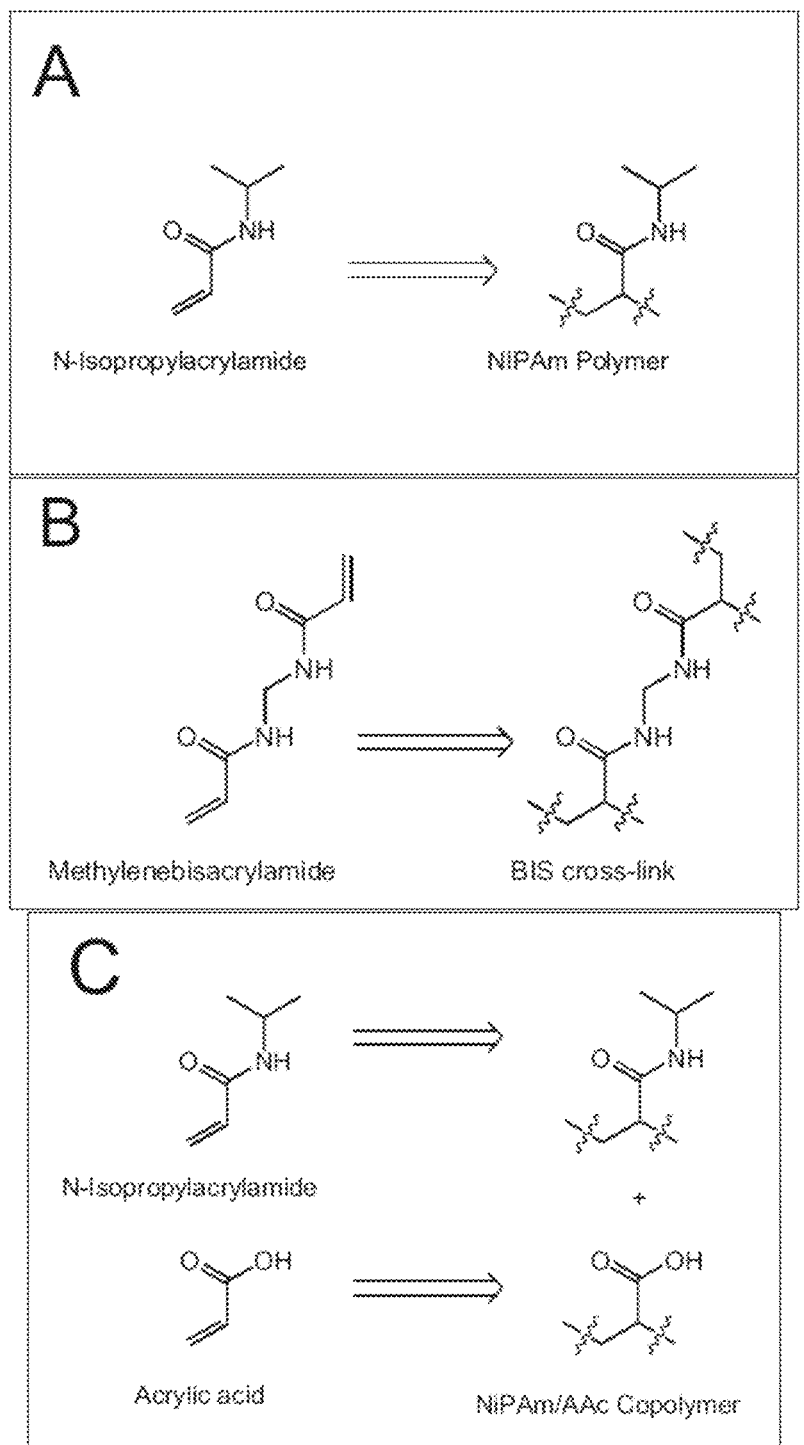
FIG. 1. Chemical composition of particles. Structure of (A) N-isopropylacrylamide (NIPAm) and its polymer, (B) methylenebisacrylamide and (C) NIPAm and acrylic acid and their polymers.

The present invention provides capture particles for harvesting biomarkers as wells as methods for using those particles. The capture particles of the present invention are capable of selectively selecting specific biomarkers from a mixture, after which the capture particles are removed from the mixture and the biomarkers are released from the capture particles.

In certain embodiments of the invention, the capture particles have one or more of the following characteristics: a) an ability to select the size and/or mass of the molecule to be captured, b) an ability to select the affinity properties of the molecule to be captured, and/or c) an ability to capture and/or release the desired molecule in response to a physical or chemical treatment. The particles of the present invention may accomplish this task in microvolumes, eliminating the need for the conventional multi-step procedures requiring, e.g., affinity columns, reverse phase columns and molecular sieve steps. The characteristics of the capture particles depend on the materials used to construct the capture particles. Examples of certain types of capture particles made from certain materials are set forth herein, however, it will be obvious to one of skill in the art that there are other combinations and variations of capture particles not explicitly set forth in this specification that have characteristics which can be determined from the way they are constructed and which fall within the scope of the claims set forth below.

Throughout this description, the harvesting of biomarkers or other analytes will be described. The capture particles and methods of the present invention can be adapted to harvest any type of molecule or compound of interest, both biomarkers produced by a living source or other analytes. It certain embodiments of the invention, the analyte to be harvested may be a metabolite, protein, RNA, micro RNA, DNA glycoprotein, lipid, glycolipid, proteolipid, hormone, cytokine, growth factor, biomarker, drug compound, synthetic organic compound, volatile odorant, toxicant or pollutant. It should be apparent to one of skill in the art that the present invention is not limited in any way to the harvesting of specific types of molecules and that molecules from any source present in any type of mixture may be harvested using the compositions and methods of the invention.

In certain embodiments, the capture particles of the present invention can be comprised of a molecular sieve material. By this, it is meant that the material is porous, lattice-like, honeycombed, or has other properties that permit analytes of a defined molecular mass or weight to enter. The size of the sieve pore is a determinant of whether the analyte can penetrate the capture particle. The particle, itself, can be of any suitable size, e.g., 1 nm or less; from about 1 nm-100 µm; from about 5 nm-50 µm; from about 10 nm-20 µm; from about 10 nm-10 µm; including any and all values in between. The particles of the present invention may have any suitable shape, including, but not limited to, spheres, tubes, branched structures, polyhedrons and micro-fluidic valves.

The sieve materials used in constructing the capture particles of the present invention may be designed so as to allow only analytes of a certain size to enter the capture particles. The size cutoff of the capture particles will be dependent on the manner in which the particles are to be used. The cutoff size, as used herein, is meant to describe the approximate size of an analyte which is able to enter the capture particle. For example, molecular weight (MW) cutoff size of 50 kDa means that molecules of approximately 50 kDa or less in size will be able to enter the capture particles, while molecules of approximately more than 50 KDa will be excluded from the particles. In certain embodiments, the particles may have a MW cutoff size of from about 5 kDa to about 100 kDa, although particles having other MW cutoff sizes outside of this range are also contemplated. As described herein, the capture particles of the present invention may be made of "smart" materials capable of changing size in response to stimuli. In such cases, the MW cutoff size of the particle may change as the size of the particles changes, e.g. a particle may have a specific MW cutoff size under certain conditions and a different MW cutoff size under other conditions.

A feature of the capture particles of the present invention is their ability to "trap" or sequester an analyte once it has entered the particle. Trapping is achieved by using sieve materials which are capable of contracting and/or expanding in response to a physical or chemical treatment for making the particles. For example, materials can be utilized which, when subjected to a chemical or physical treatment, contract or shrink, thereby trapping the analyte inside. Such materials may be referred to as "smart materials" which have the ability to change shape or size by subject to a physical or chemical treatment.

Any material having these properties can be utilized without restriction to make the capture particles of the present invention. In certain embodiments, these materials are polymers made of: acrylamide and derivatives thereof, N-isopropylacrylamide (e.g., Jones and Lyon, *Macromolecules*, 36:1988-1993, 2003; Jones and Lyon, *Macromolecules*, 33:8310-8306, 2000) and other N-alkyl substituted acrylamides; N,N-methylenebisacrylamide, N,N-cystaminebisacrylamide, N-vinylalkylamides, acrylic acid, methacrylic acid, allylamine, styrene, benzyl glutamate, 2-ethylacrylic acid, 4-vinylpyridine, silicone, hydroxyethyl methacrylate, ethylene oxide, butylenes terephthalate, 2-acrylamido-2-methyl-1-propanesulfonic acid, vinylpyrrolidone, and ethylene-vinyl acetate. In other embodiments of the present invention, the capture particles may be made of biodegradable polymers made up of lactide, glycolide, caprolactone, and hydroxyalkanoate. In still other embodiments of the present invention, the polymers may be made up of chitosan, hyaluronic acid, starch, cellulose and agarose. The polymers used to make the capture particles of the present invention mayor may not be made up of crosslinkable units. In the case of crosslinkable polymers, the crosslinks may be formed either permanently or reversibly. The polymers contemplated by the present invention may be polymers having a single repeating unit or may be co-polymers having two or more monomer units which are included in the polymer.

Other examples of materials used may be ferroelectric liquid crystalline elastomers; piezoelectric polymers; "smart" hydro gels, gels, ceramics, alloys, and polymers, etc. Other examples of suitable materials may be found in Galaev et al., Pages 835-849; Zentel; Pages 850-860; Harrison and Ounaies, Pages 860-873; in *Encyclopedia of Small Materials*, Volumes 1-2, Edited by, Schwartz, Mel© 2002 John Wiley & Sons. Examples of other materials suitable as sieving materials are woven or cross-linked nanowires, carbon nanotubes, metal colloids, clatherins, collagen, modified polysaccharides, silicon, silica, linked peptides comprised of amino acids, polymers composed of nucleic acids (see, e.g. Chittimalla et al., *J Am. Chem. Soc.*, 2005, 127 (32), 11436-41), amino acid polymers, lipids (see, e.g. *Advanced Drug Delivery Reviews, Lipid Nanoparticles: Recent Advances*, 2007, 59 (6), 375-530), self-assembled viruses, and self-assembled proteins. The capture particles can be prepared routinely by methods known in the art or as described in any of the above-mentioned references.

Physical and/or chemical treatments that may be utilized to contract and/or expand the sieve material include thermal, electrical, magnetic, ultrasound, pressure, radiant, laser, osmotic, pH, salt, enzymatic, oxidation/reduction, dehydration/rehydration, ultraviolet, radiation, high intensity red light, and similar treatments as are known in the art.

The sieve material can reversibly or non-reversibly contract or shrink. For example, the capture particles can be placed in a mixture where the analytes are permitted to penetrate, and then non-reversibly shrunk to capture the analyte. This could be useful where the objective is to remove a contaminant from a solution, and it is not necessary to analyze or further evaluate the nature of the captured analyte, thus not requiring it to be expanded. Alternatively, non-reversible capture particles can be broken apart by sonication or other disruptive forces which destroy the integrity of the particle.

The capture particles can further comprise an attractant capable of attracting and interacting with a biomarker. The attractants of the present invention may be any substance which is capable of specifically interacting with an analyte of interest. In certain embodiments, the attractant is an affinity ligand and may be: antibodies and derivatives thereof (e.g., Fab fragments and single-chain antibodies); binding proteins and peptides (e.g., receptors or fragments thereof for specific ligands and polyhistidine peptides), including modified proteins; binding pairs (such as streptavidinlbiotin); substrates; metals; chelating agents; nucleic acids; aptamers; enzyme-binding pockets; lectins, calixarenes for the uptake of small molecules; metals or metal salts (e.g. Fe for heme groups, $TiO_2$ for phosphorylated peptides and proteins); affinity dyes; pharmaceutically active compounds; peptides and fullerenes, lipophilic compounds, aromatic compounds and/or an affinity group that is specific for an analyte of interest. The capture particles may also be formed using molecular imprinting techniques, as are well known in the art. In these embodiments of the present invention, the capture particles may be imprinted to bind specific molecules or families of molecules In certain other embodiments of the invention, the attractant may be a chemical moiety capable of interacting chemically or electrostatically with the analyte. In these embodiments of the invention, the attractant may include a carboxyl group, amine group, lipid, phosphate group, amide group, hydroxyl group, ester group, acrylic group, thiol group, acrylic acid, hydrophobic surface, hydrophilic surface or any other moiety capable of interacting chemically or electrostatically with the analyte.

The attractants can be associated with the capture particle in any suitable way. For example, they can be used as a nucleus or core around which the sieve material is overlayed or deposited/nucleated in order to form the capture particle; they can be directly incorporated into the sieve material prior to forming the particle (i.e. where the attractant is a component of the sieve material); they can be conventionally coupled (covalently or noncovalently) to the pore surfaces of the sieve material; etc. The attractants can also be loaded into the capture particle by expanding the sieve material through appropriate physical or chemical treatment to reach a porosity that is large enough to admit the ligand, and then contacting the sieve material with the attractant under conditions effective for it to enter the particle. Once the particle is loaded with the attractant, it can be shrunk by appropriate physical or chemical treatment, thereby reducing the sieve material's porosity, such that target analytes are still able to penetrate the particle, but larger analytes are excluded. The sieve porosity can be reduced after the attractant loading step to pore size which is small enough to block the affinity ligand from diffusing out, making it unnecessary to link the attractant to the sieve material. However, if desired, coupling processes can be used to link the attractant to the sieve material.

Capture particles baited with affinity ligands provide an analyte selection step, in addition to selection for analyte size or mass. For example, a capture particle can be expanded to allow analytes to penetrate into it, and then the analytes can be further selected by their ability to specifically bind to an affinity ligand associated with the capture particle. After the binding step is achieved (e.g., after equilibrium is reached), the particles can be separated and subjected to washing steps to remove unbound non-target analytes, and then optionally shrunk by a chemical or physical treatment.

In certain embodiments of the invention, the attractant is a component of a sieve material. For example, the sieve material may be a co-polymer having monomeric units that have an electrostatic charge. In certain embodiments, the co-polymer is made up of uncharged structural monomer units and affinity monomer units, so that the sieve material itself is capable of attracting an analyte to be captured. In certain embodiments, the affinity monomer units may be positively or negatively charged so that the sieve material has an overall electrostatic charge. In these embodiments, is also contemplated that the charged monomeric units may be such so that their charge can be changed by changing the environment of the sieve material, e.g. changing the pH or temperature of the media surrounding the capture particles. In these embodiments, the capture particles provide both size and affinity selection of analytes.

In certain embodiments where the sieve material is a charged co-polymer, the charged monomeric units may have moieties that allow them to be charged under certain conditions. For example, negatively charged monomers may have carboxylic acid groups, hydroxyl groups, thiol groups, phosphate groups or other groups capable of carrying a negative charge. In certain embodiments of the invention, the negatively charged monomer is acrylic acid or another monomer with a carboxylic acid group. Positively charged monomers may have amine, amide groups or other groups capable of carrying a positive charge. In certain embodiments of the invention, the positively charged monomers are allylamine or chitosan.

In other embodiments of the invention where the sieve material is a co-polymer, affinity monomer units may be integrated into the sieve material that allow for attraction of various type of analytes. For example, co-polymers may be integrated with monomers having: affinity dyes having affinity for proteins and peptides; boronic acid groups having affinity for carbohydrates, nucleic acids and glycopeptides or glycoproteins; cyclodextrins having affinity for small molecules; calixarenes having affinity for small molecules; porphyrin groups having affinity for metal ions; and aliphatic groups having affinity for lipids.

In certain embodiments of the present invention the sieve material is an N-isoproylacrylamide (NIPAm), acrylic acid (AAc) copolymer whose pendant carboxylic acid ($CO_2H$) groups are functionalized with a wide range of amino or alcohol terminated molecules. These molecules can include alkanes, other greasy moieties to capture the lipid content of the solution, or dyes. In certain other embodiments of the present invention, the particles have a core made of a NIP Am AAc co-polymer that is surrounded by a shell polymer layer made up of only NIP Am.

The capture particles may also further comprise detectable labels. Detectable labels may be any moiety or substance that can be detected by any means. These include quantum dots, fluorescent labels, enzymes, magnetic particles, etc. The detectable label can be associated with any region of the capture particle, including its pores and exterior surface.

Detectable labels are useful in a number of ways, including for sorting different classes of capture particles. For example, different classes of capture particles can be produced, where each class possesses a different characteristic (e.g., a different pore size and/or a different attractant), and each carries a different detectable label associated with each class of particles. This enables the property of the particle class (e.g., able to bind to a specific attractant) to be identified by determining which detectable label it bears. For instance, a particle with a single chain antibody for PSA can be labeled with FITC, and a particle containing an antibody for a-Methylacyl-CoA racemase (AMACR) can be labeled with TRITC. After performing the entrapment step, the particles can be sorted by flow cytometry using fluorescent-activated cell sorting, separating the PSA-containing particles from the AMACR-containing particles. In other embodiments, the capture particles can be functionalized with lipophilic carbocyanine dyes and then their lipid content can be separated using thin layer chromatography.

Capture particles can be moved in solution or other media by the application of electrical fields, magnetic fields, through the use of laser tweezers, or by their affinity with solvent. If the capture particles have an overall electric charge, they may be moved by application of an electric field. This may be especially applicable when the sieve material has been modified so as to have an electrostatic charge. For example, an electric field can be applied across a medium containing negatively charged capture particles, and the capture particles would move towards the positive electrode of the device applying the electrical field.

The capture particles may also be modified to have magnetic moieties that are attracted to a magnet. In certain embodiments of the present invention, this may be done by forming the sieve material around a magnetic core, such as a $Fe_3O_4$ core. In other embodiments, the surface of the capture particles may be fully or partially coated with magnetic nanoparticles (see, e.g. Wong et al., *J Magnetism and Magnetic*

*Materials*, 2007, 311 (1), 219-23). It is further contemplated that co-polymers may be formed having magnetic elements directly incorporated into the polymers.

It is also contemplated that the capture particles may be modified to have surface markers that can be easily bound by specific targets, e.g. the particles may have biotin, glutathione-S-transferase or 6-histidine tags that can be bound by streptavidin, glutathione, and nickel substrates respectively. The particles can also be formed using reversible crosslinkers such as those formed from disulfide bonds that can be reversed by DTT. In these embodiments of the invention, a solution containing capture particles may be mixed with beads having a suitable substrate, for example, biotin labeled particles may be mixed with streptavidin labeled beads. After being allowed to bind to one another, the beads could be removed from the solution using centrifugation or other techniques known in the art, bringing the capture particles with them.

Certain embodiments of the invention relate to solution-phase capture particles and methods of using them to isolate analytes from a sample having one or more of the following steps, e.g., contacting a sample comprising analytes with solution-phase capture particles under conditions effective for the capture particles to reversibly and selectively trap analytes of a defined molecular mass or particle size, where the capture particles are made with a molecular sieve material which is capable of reversibly trapping and releasing an analyte of a defined particle size or molecular mass.

The capture particles of the present invention may allow for the protection of analytes from degradation by proteases and other factors. The capture particles may do this by excluding the proteases from the particle by the size cut-off and/or the affinity characteristics of the particle. The capture particles may also prevent proteases from degrading analytes because the analytes and proteases are so tightly bound as to prevent the steric alignment necessary for the protease to cleave the analyte. In these cases, even though the protease is capable of entering the capture particle, the analyte remains intact.

The capture particles of the present invention may also be used for concentrating low abundance analytes from a fluid. If an analyte is present in a fluid at a low concentration, the capture particles of the present invention may be used to harvest the analyte from the original fluid. After the analyte is harvested, it may then be released into a second fluid having a smaller volume. In this way, analytes having concentrations below the limits of detection of various analytical methods in their original fluids may be concentrated so that they have a concentration that can easily be detected and analyzed.

In certain embodiments of the present invention, the capture particles described may be part of kits which may be used for isolating and/or identifying an analyte. The kits may have any type of collection device for collecting the solution or other type of mixture containing the analyte. In some embodiments, the collection device is a container, such as a vacutainer, tube, cartridge or micro fluidic device. It is contemplated that the capture particles may be present in the container, or, alternatively, a layer of capture particles may be formed on the container. In other embodiments, the collecting devices are sheets of fabric or polymeric material capable of containing a layer of capture particles. In these embodiments, the capture particle may be formed into a type of patch, which may be applied to a surface from which an analyte of interest is to be isolated or over which an analyte of interest passes. In one embodiment, the patch may be a patch that can be applied to the skin, allowing analytes to be isolated from the surface of the skin.

Also contemplated by the present invention is a system where particles can be continuously moved among different steps. In general:
Step 1: Capture particles are mixed with a sample comprising analytes;
Step 2: Capture particles are separated from solution phase moieties that have not been captured; and
Step 3: Analytes are eluted from particles and analyzed.

In these embodiments of the invention, the system is fully self-contained and automated so that a sample is introduced into the system and a result is obtained without requiring any other user manipulation. Such a system may be contained in a micro fluidic system or may be a larger, bench-top type system.

In general, a sample is added to a chamber containing capture particles and the analyte of interest is sequestered. The environmental conditions of the chamber may then be changed so that the capture particles are reduced in size as described herein, trapping the analytes inside. The capture particles can then be moved to a new chamber using the methods described herein, separating the analytes from the remainder of the sample.

Analysis can then be done using methods known in the art, including mass spectrometry, nuclear magnetic resonance, infrared spectroscopy, solid phase immunoassay (e.g. ELISA and the like) immunoprecipitation, colorometric assay, radiometric assay, fluorescent assay, flow bead/flow cytometry, western blotting, protein sequencing and any chemistry analytic method for analysis of metabolites, drugs, small molecules or proteins.

Beyond the solution phase capture process, the particles can also be used to coat support surfaces, to impregnate layers and to fill slabs. Other examples include coating a patch with particles held by a mesh, and applying the patch to a patient's skin to capture analytes present on and in the skin.

Any sample can be utilized without restriction, including biological fluids, such as blood, blood components, cerebral spinal fluid, lymph, celllysates, tissue lysates, stool, urine, lymph, ascites, semen, etc.; environment samples, such as soil samples or extracts, ocean, pond, or river waters; water tower and drinking water samples; samples from chemical synthetic reactions; food samples; etc. For example, the methods discussed herein can be used to detect contaminants in food, drinking water, and environment samples. Any molecule of interest may be harvested using the present invention, including, organic molecules, inorganic molecules, polypeptides, carbohydrates, nucleic acids, lipids, drugs, antibodies, ligands, lipoproteins. glycoproteins, fatty acids, glycans, derivatives thereof, and combinations thereof. Analytes include biomolecules which are shed from cell surfaces, released from cells (e.g., by exocytosis, lysis, etc.), metabolites, degradation products, protease digestion products, and the like, without limitation. In certain embodiments of the invention, the methods can be utilized to entrap molecules in a biological fluid of a low molecular weight, especially those that would be excluded from the body by normal glomerular (kidney) filtration (e.g., molecules less that 30,000 Daltons) which are soluble and free-floating in the fluid or which are associated with carrier proteins. In general, the present invention can be used to capture any analyte of interest whose detection is desired. The particles can be used in solution during any chemical reaction to selectively capture reaction products and therefore lower products concentration in solution. This can enable the chemical reaction to go to completion or to drive the chemical reaction to completion by sequestering one or more reaction species as they accumulate over time. With respect to body fluids, the capture particles of the present invention can also be used to detect exogenous molecules, i.e., is a molecule that was introduced into the body of the subject from whom the sample was obtained. Exogenous molecules can be actively or passively introduced into the subject. Examples of exogenous molecules include molecules present in, or in the form of, drugs, foods, tobacco, environmental products and contaminants (e.g., pesticides, carbon monoxide, etc), and essentially any molecule that enters the subject body through any route. Exogenous molecules also include their metabolites, by-products, and degradation products as processed or transformed in the body. The particles can also be used as a tool to clear toxins from the blood. The particles can be applied for dialysis of blood by clearing urea or to eliminate cholesterol in excess to prevent heart attacks.

It is also contemplated that different populations of capture particles can be used at the same time, each having different characteristics with respect to the molecule species they are able to capture. The different populations can be univocally tagged, e.g. with fluorescent dyes, and can afterwards be separated, e.g. with flow cytometry. This strategy enables a total extraction and separation of multiple species to be performed in a single step.

Further Embodiments of the Present Invention

Nanoparticle Technology for Biomarker Enrichment and Preservation

In order to directly address the challenges of low abundance and preservation, in certain embodiments, this invention aims to create and evaluate "smart" nanoparticles that harvest (accumulate) selected classes of proteins in solution when added to complex mixtures of proteins such as plasma. The deliverable technology will be novel porous harvesting particles that have a unique structure capable of sorting molecules in solution based on both size and/or affinity. Moreover, the porosity of the particles may be thermally modifiable such that captured analyte (e.g. proteins) can later be released for analysis. In addition, the proteins or chemical entities captured within the particles may be protected from degradation by enzymes or microbial growth.

This proposed technology can address the need for a means to enrich, isolate, and preserve low-abundance proteins and peptides in blood, urine and tissues. Such low-abundance molecules are expected to contain the most specific information about the state of a small disease lesion. In one embodiment the proposed technology consists of smart nanoparticles that can be pre-dispensed into a collection tube. Once the nanoparticles are suspended within the body fluid, or tissue lysate for example, the particles automatically (in one step) perform affinity chromatography and/or size exclusion chromatography in solution. The proteins and other metabolites (candidate biomarkers) captured within the smart particles can be therefore bonded and/or sequestered and protected from substantial degradation. By tuning the pore size and affinity properties of the smart particle populations, highly specific subsets of biomarkers can be captured and enriched from the entire volume of the procured fluid. This will enable room-temperature preservation and enrichment of low-molecular weight proteomic biomarkers. Following transport of the collection tube to the analysis lab, the nanoparticles can be easily isolated, so that the bound/sequestered biomarker cargo can be released for characterization using any analytical technique. In an alternative method, the biomarkers may be accessed via destructive treatment of the nanoparticles.

This technology can be of low cost and applicable in the routine clinical setting for seamless collection and immediate preservation of blood biomarkers. This transcends the large research hospital environment and extends most acutely to the private practice, where most patients receive therapy. The fabrication of large quantities of uniform "smart" one-micron-sized nanoparticles is certainly feasible, while other sizes larger or smaller are also possible and equally applicable. As described below, the particles can capture, accumulate, and purify labeled subsets of molecules from complex mixtures of molecules, such as serum.

Rationale for Choosing Smart Particles for Biomarker Harvesting

Thermoresponsive polymer gels are commonly referred to as 'smart gels' and display a controllable, nonlinear response to changes in local solution temperature, pH or external energy application (Saunders, et al., 1999 *Advances in Colloid and Interface Science* 80, 1; Pelton, 2000, *Advances in Colloid and Interface Science* 85, 1). Such polymers are comprised of crosslinked chains that undergo a thermodynamically favored phase separation leading to a change in gel volume (Tanaka, et al., 1979, *Phys. Rev. Lett.* 42, 1556; Tanaka, et al., 1978, *Phys. Rev. Lett.* 40, 820). The gels can be synthesized in bulk to take on the shape of the container or may be synthesized into particles ranging in diameter from 4 nm-100 µm (Tanaka, et al., 1980, *Phys. Rev. Lett.* 45, 1636; Tanaka, et al., 1985, *Phys. Rev. Lett.* 55, 2455). In each case, the internal structure of the material is composed of flexible chains creating a soft, porous structure that can reversibly expand or contract according to the local conditions of the solution. An example of a "smart" polymer is poly(N-isopropylacrylamide) (pNIPAm), which has a lower critical solution temperature (LCST) of 31° C. in water (Jones, 2003, *School of Chemistry and Biochemistry*, Georgia Institute of Technology, Atlanta, Ga., p. 193). Below this temperature, the polymer matrix is swollen with solvent molecules, where hydrogen bonding occurs between the water and amide groups along the polymer backbone (Jones, 2003, *School of Chemistry and Biochemistry*, Georgia Institute of Technology, Atlanta, Ga., p. 193). As the temperature is increased above the LCST, hydrogen bonds are broken and water is excluded from the internal matrix, while hydrophobic interactions begin to dominate between the isopropyl groups, leading to a decrease in overall volume. This technology can be applied to separating biomarkers for identification.

One aspect of the present invention describes a molecular sieve portion of the capture-particles while another aspect pertains to an analyte binding (bait capture) portion. It is feasible to combine bait capture with molecular sieving into a single particle. A common means of fractionating complex mixtures of proteins is to use two classes of sequential chromatographic steps based on affinity and molecular sizing (Adkins, et al., 2002, *Mol Cell Proteomics* 1, 947). Analysis of a complex and highly concentrated mixture such as plasma usually starts with dilution of the sample and removal of high-abundance proteins such as albumin prior to chromatography and gel electrophoresis. The smart particle technology disclosed herein accomplishes both steps of the separation without the use of chromatography or dilution. More specifically, added selectivity is enabled through the addition of bait molecules into the particle that bind/sequester a restricted population of biomarkers. Acrylic acid (AAc), for example, can be integrated into the particle and function as a tunable affinity resin. For example, at low pH (3.5), the AAc within the particle will be predominately protonated, bearing a positive charge at that pH. At higher pH conditions, the AAc moieties will be either partially or predominately deprotonated, which will create an intrinsic, charge based affinity element for positively charged proteins. By integrating AAc into the microgel, both the charge properties and the pore size of the particles provide a means to doubly fractionate proteins from complex mixtures like serum.

Another aspect of the invention deals with preservation by sequestration/binding of analytes therefore allowing one to stabilize analytes (e.g candidate biomarkers) in solution at room temperature. This can accomplished by their sequestration within the porous nanoparticles. It is hypothesized that proteins or molecules sequestered within the nanoparticles will not be available for access by solution phase degradative enzymes. Such enzymes may not be able to penetrate the pores of the particle because of their larger size.

Moreover, the affinity capture and immobilization of the candidate biomarker molecule will hinder the 3-D availability of the biomarker molecule such that the enzyme substrate complex can not functionally form within the particle. This concept is somewhat analogous to the stabilization of proteins by precipitation or precipitation fixation. Applying capillary electrophoresis and mass spectrometry sequencing, we can study the degradation induced by exogenous serine or metalloproteinases, and compare the rate of fragmentation of proteins sequestered in particles versus those free in solution. Starting with defined mixtures of known and pre-characterized, or pre labeled proteins, we can progress to protein capture and stabilization within human serum and plasma reference samples.

Capture-Particles

In certain embodiments, the present invention provides a method and composition for separating and capturing molecular species from samples. In one embodiment of the invention, smart particles which have the ability to specifically capture molecular species having a defined molecular size, mass, and/or affinity characteristic are used to isolate molecules of interest from a sample typically containing a plurality of different molecular species with varying sizes. The particles can be added to the sample and then utilized to capture the molecular species of interest.

The particles can have one or more of the following functionalities: a) an ability to select the size, mass, and/or affinity property of the molecule to be captured, and/or b) an ability to capture and/or release the desired molecule in response to a physical or chemical treatment. The particles can accomplish this task in microvolumes, eliminating the need for the conventional multi-step procedures that utilize affinity columns, reverse phase columns, and other standard purification reagents and devices. Moreover, different classes of capture-particles can be used, each having different characteristics with respect to the molecule species they are able to capture, thus enabling a total extraction profile of multiple species to be performed in a single step.

One aspect of the inventions provides solution-phase capture-particles and methods of using them in isolating analytes from a sample, said method comprising one or more of the following steps including contacting a sample comprising analytes with solution-phase capture-particles under conditions effective for said capture-particles to selectively and optionally reversibly, trap analytes of a defined molecular mass or particle size, wherein said capture-particles comprise a molecular sieve material which is capable of trapping and optionally releasing an analyte of a defined particle size or molecular mass. Other aspects of the present invention, as described in more detail below, also employ specific capture-particles which non-reversibly trap analytes.

Samples

Any sample can be utilized without restriction, including biological fluids, such as blood, blood components, cerebral spinal fluid, lymph, cell lysates, tissue lysates, stool, urine, lymph, ascites, semen, ocular vitreous, etc.; environment samples, such as soil samples or extracts, ocean, pond, or river waters; water tower and drinking water samples; samples from chemical synthetic reactions; food samples; food processing samples (eg., from poultry processing plants), etc. For example, the methods can be used to detect contaminants in food, drinking water, and environment samples.

Analytes

The term "analyte" refers to any molecule of interest, including, organic molecules, inorganic molecules, polypeptides, carbohydrates, nucleic acids, lipids, derivatives thereof, and combinations thereof. Analytes include biomolecules which are shed from cell surfaces, released from cells (e.g., by exocytosis, lysis, etc.), metabolites, degradation products, protease digestion products, etc., without limitation. In one aspect of the invention, the methods can be utilized to entrap molecules in a biological fluid of a low molecular weight, especially those that would be excluded from the body by normal glomerular (kidney) filtration (e.g., molecules less that 30,000 Daltons) which are soluble and free-floating in the fluid or which are associated with carrier proteins. In general, the present invention can be used to capture any analyte of interest whose detection is desired including but not limited to sizes less than about 60,000 Da, less than about 50,000 Da, less than about 40,000 Da, less than about 30,000 Da, less than about 20,000 Da, less than about 10,000 Da, less than about 8,000 Da, less than about 6,000 Da, less than about 4,000 Da, less than about 2,000 Da, less than about 1,000 Da, including all individual values within each stated range.

With respect to body fluids, the capture-particles of the present invention can also be used to detect exogenous molecules, i.e., a molecule that was introduced into the body of the subject from whom the sample was obtained. Exogenous molecules can be actively or passively introduced into the subject. Examples of exogenous molecules include molecules present in, or in the form of, drugs, foods, tobacco, environmental products and contaminants (e.g., pesticides, carbon monoxide, etc), and essentially any molecule that enters the subject body through any route. Exogenous molecules also include their metabolites, by-products, and degradation products as processed or transformed in the body.

The capture particles can be utilized in any environment, including in vivo, ex vivo, and in vitro. For example, the particles can also be used as a tool to clear toxins from the blood in an in vivo or ex vivo context. For example, the particles can be utilized to remove toxic wastes from the blood, such as creatinine and urea, replacing the need for conventional dialysis.

Molecular Sieve Material

The capture-particles of the present invention can be comprised of a molecular sieve material (or molecular sieve portion). By this, it is meant that the material is porous, lattice-like, honeycombed, or has other properties that permit passage of analytes of a defined molecular mass or weight while excluding others. The size of the sieve pore is a determinant of whether the analyte can penetrate the capture-particle. The particle, itself, can be of any suitable size, e.g., less than about 10 μm, between about 10 μm and about 1 μm, between about 1 μm and about 100 nm, between about 1 nm and 100 nm, between about 5 nm and about 50 nm; between about 10 nm and about 20 nm; between about 10 nm and 1 nm; including all individual values within each recited range.

Pores in the sieve material can be designed based on the provided methods to diameters necessary for exclusion of unwanted molecules. Average pore sizes of between about 2 to about 20 nm, 1 nm to 1 μm, 1 nm to 10 nm, 1 nm to 50 nm, 10 nm to 50 nm, 50 nm to 100 nm, 10 nm to 200 nm, 50 nm to 500 nm, 1 nm to 10 nm, 1 nm to 5 nm, and other ranges are envisioned.

An optional feature of capture-particles is its ability to "trap" an analyte once it has entered the sieve material. The trapping may be achieved by using sieve materials which are capable of contracting and/or expanding in response to a physical or chemical treatment. For example, materials can be utilized which, when subjected to a chemical or physical treatment, contract or shrink, thereby trapping the analyte inside. Such materials can also be referred to as "smart materials" which have the ability to change shape or size by subject to a physical or chemical treatment. Any material having this property can be utilized without restriction, including, but not limited to, e.g., polyacrylamide and derivatives thereof; poly (N-isopropylacrylamide (e.g., Jones and Lyon, *Macromolecules,* 36:1988-1993, 2003; Jones and Lyon, *Macromolecules,* 33:8310-8306, 2000) and other N-alkyl substituted acrylamides; poly(N-vinylalkylamides); poly(methacrylic acid); poly(benzyl glutamate); poly(2-ethylacrylic acid); poly(4-vinylpyridine); ferroelectric liquid crystalline elastomers; piezoelectric polymers; "smart" gels, ceramics, alloys, and polymers, etc. See, also, e.g., Galaev et at., Pages 835-849; Zentel; Pages 850-860; Harrison and Ounaies, Pages 860-873; in *Encyclopedia of Smart Materials*, Volumes 1-2, Edited by, Schwartz, Mel© 2002 John Wiley & Sons. The capture-particles can be prepared routinely as known in the art or described in any of the above-mentioned references.

In one embodiment of the present invention the capture-particles do not contain any poly(N-isopropylacrylamide) constituent. Furthermore, capture particles in this embodiment also exclude poly(N-isoproplyacrylamide-co-acrylic acid.)

Physical or Chemical Treatment of Sieve Material

Physical and/or chemical treatments that can be utilized to contract and/or expand the sieve material can comprise thermal, electrical, magnetic, ultrasound, pressure, radiant, laser, osmotic, pH, salt, enzymatic, oxidation/reduction, dehydration/rehydration, ultraviolet, radiation, high intensity red light, treatments.

The sieve material can reversibly or non-reversibly contract or shrink. For example, the capture-particles can be placed in a solution where the analytes are permitted to penetrate, and then non-reversibly shrunk to capture the analyte. This could be useful where the objective is to remove a contaminant from a solution, and it is not necessary to analyze or further evaluate the nature of the captured analyte, thus not requiring it to be expanded. Alternatively, non-reversible capture-particle can be broken apart by sonication or other disruptive forces which destroy the integrity of the particle.

In one embodiment the capture-particle is capable of expanding and contracting to allow for capture and/or sequestration of an analyte.

In another embodiment, the capture-particle does not expand or contract to any significant degree to enable increased or reduced uptake of an analyte. That is the volume of the particle is substantially fixed. Examples of such capture particles include particles comprising viral proteins, Clatherin, carbon nanotubes or species which do not permit the expansion/contraction described previously. An example illustrating preparation of a polygonal structure from Clatherin is described in Jaarsveld, et al., *Biochemistry* 1981, 20, 4129-4135 hereby incorporated by reference.

Analyte Binding (Affinity) Portion

The capture particles can comprise surface protein properties for selective analyte binding and/or can be modified by the attachment of moieties that confer such binding properties.

The capture-particles can further comprise an analyte binding, affinity ligand or "bait." Such terms can refer to substances which are capable of specifically attaching to an analyte of interest. Typical examples include, but are not limited to antibodies and derivatives thereof (e.g., Fab fragments and single-chain antibodies); binding proteins (e.g., receptors or fragments thereof for specific ligands); binding pairs (such as Streptavidin/biotin); substrates; metals; chelating agents; nucleic acids; aptamers; enzyme-binding pockets; lectins; and/or an affinity group that is specific for an analyte of interest. The term "specific" has a functional meaning that the affinity ligand can be use to selectively bind to an analyte of interest in a sample and distinguish it from non-target analytes. It is specific in the sense that it can be used to detect analytes above background noise ("non-specific binding"). The affinity ligand can be selected such that it has a higher affinity for the analyte of interest than other components in the sample, allowing to out-compete any native binding proteins for the analyte.

The affinity ligands can be associated with the capture-particle in any suitable way. For example, they can used as a nucleus around which the sieve material is overlayed or deposited/nucleated in order to form the capture-particle; they can be directly incorporated into the sieve material prior to forming the particle (i.e., where the ligand is a component of the sieve material); they can be conventionally coupled (covalently or noncovalently) to the pore surfaces of the sieve material; etc. The affinity ligands can also be loaded into the capture particle by expanding the sieve material through appropriate physical or chemical treatment to reach a porosity that is large enough to admit the ligand, and then contacting the sieve material with the ligand under conditions effective for it to enter the particle. Once the particle is loaded with the affinity ligand, it can be shrunk by appropriate physical or chemical treatment, thereby reducing the sieve material's porosity, such that target analytes are still able to penetrate the particle, but larger analytes are excluded. The sieve porosity can be reduced after the affinity ligand loading step to pore size which is small enough to block the affinity ligand from diffusing out, making it unnecessary to link the affinity ligand to the sieve material. However, if desired, coupling processes can be used to link it to the sieve material.

Capture-particles baited with affinity ligands provide an analyte selection step, in addition to selection for analyte size or mass. For example, a capture-particle can be expanded to allow analytes to penetrate into it, and then the analytes can be further selected by their ability to specifically bind to an affinity ligand associated with the capture-particle. After the binding step is achieved (e.g., after equilibrium is reached), the particles can be separated and subjected to washing steps to remove unbound non-target analytes, and then optionally shrunk by a chemical or physical treatment.

The capture-particles can also further comprise antibodies as an affinity portion. Other candidate affinity portions include, but are not limited to, soluble receptors, polyamine analogs, antisense oligonucleotides, RNAi polynucleotides, ribozymes, and the like. Antibodies and soluble receptors are of particular interest as affinity portions where they target analytes of interest.

Antibodies

Affinity portions include antibodies and functional equivalents thereof that specifically bind to analytes. "Immunoglobulin" and "antibody" are used interchangeably and in their broadest sense herein. Thus, they encompass intact monoclonal antibodies, polyclonal antibodies, multi specific antibodies (e.g., bispecific antibodies) formed from at least two intact antibodies, and antibody fragments, so long as they exhibit the desired biological activity.

The variable domains of the heavy and light chain of an antibody recognize or bind to a particular epitope of a cognate antigen. The term "epitope" is used to refer to the specific binding sites or antigenic determinant on an antigen that the variable end of the immunoglobulin binds. Epitopes can be linear, i.e., be composed of a sequence of amino acid residues, conformational, such that an immunoglobulin recognizes a 3-D structure, or a combination thereof.

Monoclonal and Polyclonal Antibodies

Immunoglobulins of the invention may be polyclonal or monoclonal, and may be produced by any of the well known methods in this art.

Polyclonal antibodies are preferably raised in animals by multiple subcutaneous (sc), intraperitoneal (ip) or intramuscular (im) injections of the relevant antigen and an adjuvant. It may be useful to conjugate the relevant antigen to a protein that is immunogenic in the species to be immunized. In addition, aggregating agents such as alum are suitably used to enhance the immune response.

The term "monoclonal antibody" refers to an antibody obtained from a population of substantially homogeneous antibodies. Monoclonal antibodies are highly specific, being directed against a single antigenic site. Furthermore, in contrast to polyclonal antibody preparations that typically include different antibodies directed against different determinants, each monoclonal antibody is directed against a single determinant on the antigen.

In addition to their specificity, monoclonal antibodies are advantageous in that they may be synthesized while uncontaminated by other immunoglobulins. For example, monoclonal antibodies may be produced by the hybridoma method or by recombinant DNA methods. Monoclonal antibodies also may be isolated from phage antibody libraries.

Antibody Fragments

"Antibody fragments" comprise a portion of an intact antibody, preferably the antigen-binding or variable region thereof. Examples of antibody fragments include Fab, Fab', F(ab')^2, Fv fragments, diabodies, linear antibodies, single-chain antibody molecules, and multispecific antibodies formed from antibody fragments.

Various techniques have been developed for the production of antibody fragments. Traditionally, these fragments were derived via proteolytic digestion of intact antibodies. Two digestion methodologies that are well known in the art include papain digestion and pepsin treatment. Antibody fragments may now additionally be produced directly by recombinant host cells.

Bispecific Antibodies

Bispecific antibodies of the invention are small antibody fragments with two antigen-binding sites. Each fragment comprises a heavy-chain variable domain connected to a light-chain variable domain in the same polypeptide chain. By using a linker that is too short to allow pairing between the two domains on the same chain, the domains are forced to pair with the complementary domains of another chain and create two antigen binding sites.

Methods for making bispecific antibodies are well known in the art. Traditional production of full length bispecific antibodies is based on the coexpression of two immunoglobulin heavy chain-light chain pairs, where the two chains have different specificities. Bispecific antibodies, however, may also be produced using leucine zippers.

The capture-particles can also further comprise detectable labels. By the term "detectable label," it is meant any moiety or substance that can be detected by any means. These include, quantum dots, fluorescent labels, enzymes, magnetic particles, etc. The detectable label can be associated with any region of the capture-particle, including its pores and exterior surface. Detectable labels are useful in a number of ways, including for sorting different classes of capture-particles. For example, different classes of capture-particles can be produced, where each class possesses a different characteristic (e.g., a different pore size and/or a different affinity-ligand), and each carries a different detectable label associated with each class of particles. This enables the property of the particle class (e.g., able to bind to a specific antigen) to be identified by determining which detectable label it bears, For instance, a particle with a single chain antibody for PSA can be labeled with FITC, and a particle containing an antibody for {alpha}-Methylacyl-CoA racemase (AMACR) can be labeled with TRITC. After performing the entrapment step, the particles can be sorted by flow cytometry using fluorescent-activated cell sorting, separating the HA-containing particles from the AMACR-containing particles.

Purification Methods

The capture particles of the current invention may be used in purification protocols to isolate analytes of interest from samples. As described above, the capture particles allow for purification of analytes based on size and affinity and this invention allows for quick isolation of analytes of interest from samples in order to preserve and study the analytes of interest. These analytes are preserved in the capture particles in order to prevent degradation from enzyme or other molecules in the sample.

Diagnostic Methods

The current invention also include a method of diagnosing a disease by contacting a sample comprising analytes with solution-phase capture-particles under conditions effective for the capture-particles to selectively bind analytes of a defined molecular mass, particle size, or defined affinity and then identifying the analytes selectively bound to the capture particles. The presence of analytes in the sample at identified concentrations would be characteristic of a disease state. Detecting the presence of an analyte could be done using methods well known to one of skill in the art such as enzyme-linked immunosorbant assay (ELISA), mass spectrometry, radioimmunoassay (RIA), micro array methods, immunoflourescence. northern blots, polymerase chain reaction (PCR), and in situ hybridization.

Kits

In certain kit embodiments, the capture particles are provided in a form suitable for use in purification or diagnostic methods. Kits generally provide the capture particles as well as reagents, instructions, and the necessary products for performing the purification or diagnostic method. These kits are envisioned for use by doctors in a medical setting to store samples or by others to begin purification and isolation of serum analytes.

The disclosure of all publications cited above are expressly incorporated herein by reference in their entireties to the same extent as if each were incorporated by reference individually.

In some embodiments the capture-particles comprise a molecular sieve portion and an analyte binding portion wherein the molecular sieve portion, analyte binding portion or both further comprise a cross-linked region having modified porosity.

In some embodiments, the capture particles comprise a molecular sieve portion and an analyte binding portion wherein the molecular sieve portion, analyte binding portion or both comprise pore dimensions sufficient to exclude molecules larger than about 60 kDa In one embodiment, said analyte binding portion comprises at least one type of moiety capable of chemically or electrostatically binding or sequestering an analyte. Accordingly, the analyte is effectively retained in a region within the capture-particle. Forces between the analyte and the analyte binding region may be that of, covalent bonding, van der waals forces, hydrophobic-hydrophobic, hydrogen bonding, hydrophyllic attraction, ionic attraction, or any combination thereof.

In another embodiment, the capture particles comprise pore sizes of between about 2 and about 20 nanometers with all individual values in between.

In another embodiment, the capture particles comprise pore sizes of less than about 100 nm including all individual values within this range.

In another embodiment, the capture particle comprises pore sizes dimensioned to exclude molecules having sizes greater than about 60 kDa.

In another embodiment, the capture particle comprises pore sizes dimensioned to exclude albumin.

In another embodiment, the capture particle comprises pore sized sufficiently large to permit passage of molecules of 1404 Da size while excluding albumin, molecules having sizes greater than about 60 kDa or both.

The entire disclosure of all applications, patents and publications cited above, and in the figures are hereby incorporated by reference in their entirety. Certain embodiments of the invention are set forth in the non-limiting examples below. It will be apparent to one of skill in the art that there are other embodiments not explicitly set forth in this specification that are within the scope and spirit of the invention as claimed.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1

Capture Particles Incorporating N-Isopropylacrylamide (NIP Am)

Capture particles incorporating N-Isopropylacrylamide (NIPAm) and N,N-methylenebisacrylamide (BIS) were created by surfactant-free precipitation polymerization. BIS was used as the crosslinker, and the BIS:NIP Am monomer ratio determined the resultant network density and thus the average pore size. Further, a preparation of particles containing acrylic acid (AAc) was fabricated in order to incorporate a charge-based affinity bait into the particles. N-Isopropylacrylamide (NIPAm), N,N'-methylenebisacrylamide (BIS), ammonium persulfate (APS), acrylic acid (AAc) were purchased from Sigma-Aldrich of St. Louis, Mo. Water for reactions, washing and loading will be purified with a Millipore Milli-Q water purification system to a resistance of 18 MQ and passed through a 0.2 μm filter.

The total monomer concentration (NIPAm and BIS) was 0.3 M. Particles were made using varying amounts of crosslinker during polymerization, including 2% and 5% total concentration of crosslinking agent in order to vary the pore sizes of the particles. The monomers were fully dissolved in 190 mL of water inside of a round bottom 250 mL 3-neck flask fitted with a condenser and thermometer at a medium stir rate (magnetic stirrer). The solution was heated to 70° C. over the period of 1 hour under a stream of nitrogen. When a stable maximum stir rate was achieved, the polymerization was initiated with a 1.0 mL solution of 6 mM APS. The reaction was allowed to proceed for 3 hours under nitrogen. After cooling to room temperature overnight, 0.5 mL aliquots of the micro gel solution was placed into individual 1.5 mL capacity centrifuge tubes and diluted with 1.0 mL of water. The samples were then centhfuged for 20 minutes at 23° C. and 16,100 rcf with an Eppendorf 541 SR centrifuge. The supernatant was decanted and the microgels redispersed in water, again to a volume of 1.5 mL. This process was repeated for a total of five concentration/redispersion steps. Uniformity and size range was assessed using photon correlation spectroscopy (PCS submicron particles analyzer, Beckman Coulter), Atomic Force Microscopy (AFM), light microscopy as well as uptake of fluorescent dyes with fluorescence microscopy visualization. Flow cytometry also enabled relative size to be assigned through the use of commercially available fluorescently labeled sizing particles as standards.

In order to investigate the molecular exclusion properties of the particles, particles fabricated using 2% crosslinker concentration were incubated with five molecular species: FITC (MW 389), fluorescein linked to a small peptide angiotensin II (MWI404), FITC linked to insulin (MW 3500), to streptavidin (MW 53000), and to albumin (MW 66000). In-solution separation of five types of molecules was conducted. For each of the five fluorescent molecules, 0.1 mL of purified microgels were placed into a 1.5 mL centrifuge tube. To this, 0.1 mL of molecule solution was added and mixed gently on a vortex. Fluorescence uptake by the particles was measured using a FACScan (Becton Dickinson). Experiments were conducted at different incubation times and at different concentrations of fluorescent molecules. These experiments indicated that small FITC molecules readily migrated into the particles, in as little as 10 minutes, and that the response is dose dependent. The fluorescein-labeled peptide also migrated into the particle, but with a less intense signal shift when compared with FITC, indicating that the particles have a size-mediated selectivity. For both FITC- and fluorescein-labeled peptide, the level of internalization was higher in the 2% crosslinker population of particles than in the 5% crosslinker population. This is consistent with a smaller nanopore size within the more highly crosslinked particle population, which would make internalization of the peptide more difficult. In both the 2% and 5% populations, albumin was excluded. Streptavidin and BSA were excluded from particles since there was no shift in the fluorescence signal. FITC labeled insulin was investigated both as an aqueous solution and spiked in human serum. Particles incubated with serum had a shift in the fluorescent signal that demonstrated insulin harvesting from a complex biological solution. Particles incubated with aqueous solution of FITC labeled insulin yielded a more intense fluorescent shift when compared to the serum.

SDS PAGE experiments were carried out on particles with a crossliker concentration of 2% and demonstrated insulin (MW 3500) and myoglobin (MW 17000) uptake, BSA (MW 66000) exclusion. Acrylic acid functionalized particles were incubated with a 20 mM solution of myoglobin and captured all the protein in solution, giving a much higher uptake yield when compared to plain particles.

Example 2

Electro-Transport of the Particles

Serum incubated particles with 2% crosslinker were loaded in a sample tube of centrilutor micro-electroeluter (Millipore) where a 5 mm long 30% acrylamide/bis gel slice was previously polymerized. When an electric field was created, particles migrated towards the positive electrode through the gel slice without losing their protein content.

Example 3

Hydrogel Particles

The ability of hydrogel particles to perform directly, in one step and in solution, the partition, affinity separation, concentration, and stabilization of low molecular weight proteins in serum was analyzed as a new rapid method for blood derived biomarker isolation and analysis. Hydrogels, by definition, are three-dimensional cross-linked polymeric networks that can imbibe large amounts of water (Pelton, R. *Adv Colloid Interface Sci* 2000, 85, (1), 1-33). They are usually formed through monomer polymerization in the presence of a cross-linking agent, which is typically a monomer with at least two polymerizable functional moieties. Gels can be categorized as nonresponsive (simple polymeric networks dramatically swell upon exposure to water) or responsive gels (have added functionality and display changes in solvation in response to certain stimuli such as temperature (Li and Tanaka, *The Journal of Chemical Physics* 1990, 92, (2), 1365-1371) pH, (Jones and Lyon, *Macromolecules* 2000, 33, (22), 8301-8306; Moselhy et al., *Journal of Biomaterials Science, Polymer Edition* 2000, 11, (2), 123-147) ionic strength (Duracher et al., *Colloid & Polymer Science* 1998, 276, (3), 219-231; Duracher et al., *Colloid & Polymer Science* 1998, 276, (10), 920-929) light (Sershen et al., *Temperature-sensitive polymer-nanoshell composites for photothermally modulated drug delivery*, In 2000; Vol. 51, pp 293-298; Suzuki and Tanaka, *Nature* 1990, 346, (6282), 345-347) and electric field (Tanaka et al., *Science*, 1982, 218, 467-9).

Poly (N-alkyl acrylamides) have been extensively studied with respect to their thermoresponsivity (Pelton, R. *Adv Colloid Interface Sci* 2000, 85, (1), 1-33; Inomata et al., *Macromolecules*, 1990, 23, 4887-8) with poly(N-isopropylacrylamide) (NIPAm) being one of the most strongly explored temperature sensitive hydro gels within this group. NIP Am containing particles are highly appealing for their potential biotechnological applications, because of their stability, uniformity, and versatility with regard to the ease of making physical-chemical modifications in the particles. NIP Am particles have been investigated for drug delivery slow release and targeted release, for solute desorption (Kawaguchi et al., *Colloid & Polymer Science* 1992, 270, (1), 53-57; Achiha et al., *Polym. Adv. Technol,* 1995, 6, (7), 534-540; Delair et al., *Colloids and Surfaces A: Physicochemical and Engineering Aspects* 1999, 153, (1-3), 341-353; Mattiasson et al., *Nat. Protocols* 2007, 2, (1), 213-220; Spamacci et al., *J Biomater Sci Polym Ed* 2005, 16, (12), 1557-74; Haruyuki Hiratani, *Macromolecular Bioscience* 2005, 5, (8), 728-733; Nahar et al., *Crit Rev Ther Drug Carrier Syst* 2006, 23, (4), 259-318; Wu et al., *Journal of Controlled Release* 2005, 102, (2), 361-372; Zhang et al., *Biomaterials* 2005, 26, (16), 3299-309; Woo et al., *Pharm Res* 2001, 18, (11), 1600-6; Basinska, *Macromol Biosci* 2005, 5, (12), 1145-68), interaction with cells (Achiha et al., *Polym. Adv. Technol,* 1995, 6, (7), 534-540), and coupling with oligodeoxyribonucleotides (OND) as a solid phase for hybridization (Delair et al., *Colloids and Surfaces A: Physicochemical and Engineering Aspects* 1999, 153, (1-3), 341-353). Since the size and porosity can be controlled by temperature, the use of temperature treatment to control uptake and release of chemicals has been one of the most extensively characterized application of NIP Am particles as vectors for controlled drug delivery (Spamacci et al., *J Biomater Sci Polym Ed* 2005, 16, (12), 1557-74; Haruyuki Hiratani, *Macromolecular Bioscience* 2005, 5, (8), 728-733; Nahar et al., *Crit Rev Ther Drug Carrier Syst* 2006, 23, (4), 259-318; Wu et al., *Journal of Controlled Release* 2005, 102, (2), 361-372; Zhang et al., *Biomaterials* 2005, 26, (16), 3299-309; Woo et al., *Pharm Res* 2001, 18, (11), 1600-6; Basinska, *Macromol Biosci* 2005, 5, (12), 1145-68).

In the present study, hydrogel particles containing an affinity bait and a defined porosity were developed and demonstrated to a) rapidly and in one step sequester the low molecular weight fraction of serum proteins, peptides and metabolites, b) remove and concentrate the target molecules from solution, and c) protect captured proteins from enzymatic degradation.

NIPAm based particles have been chosen because their high water content, broad range of tunable porosities, consistency and uniformity following synthesis, functional reconstitution following freeze-drying, and potential biocompatibility. By changing the percentage of cross linking agent and temperature, it is possible to control the particles size and the effective porosity. A significant advantage for the application studied here is the ability of these particles to rapidly uptake molecules because of their open structure, high water content, dual hydrophobic and hydrophilic chemical moieties that can be substituted in the polymer, and large surface area. This is a critical requirement for the goal of rapid harvesting of labile small proteins in solution and protecting the proteins from degradation. The small size, uniformity of particle dimension, and reproducibility from batch to batch, of NIP Am provide special advantages for applications in flow cytometry.

Example 4

Hydrogel Particle Synthesis and Characterization

Gel particles incorporating N-isopropylacrylamide (NIPAm) were created and evaluated for molecular sieving properties. A second class of particles containing both NIP Am and acrylic acid (AAc), NIPAm/AAc, were fabricated to incorporate a charge-based affinity bait into the particles, as shown in FIG. 1 (Pelton, *Adv Colloid Interface Sci* 2000, 85, (1), 1-33; Jones and Lyon, *Macromolecules* 2000, 33, (22), 8301-8306; Saunders and Vincent, *Advances in Colloid and Interface Science* 1999, 80, (1), 1-25). To obtain N-isopropylacrylamide (NIPAm) particles, NIPAm (1.4 g) and BIS (0.04 g) were dissolved in 150 ml of water and then filtered twice through a membrane filter (Pall Gelman Metricel). The solution was degassed under vacuum for at least 20 minutes. SDS (0.057 g) was then dissolved in the monomer solution, which was filtered again. During filtration 40 ml of water were used for transfer and washing. The solution was placed in a round bottom 250 ml 3-neck flask fitted with a condenser and thermometer at a medium stir rate (Coning magnetic stirrer). The solution was heated to 70° C. for 1 hour under a nitrogen atmosphere. A stable maximum stir rate was reached and polymerization initiated via addition of APS (0.069 g) dissolved in 10 ml of degassed water. The reaction was allowed to proceed at a temperature of 70° C. for 6 hours under nitrogen. NIP Am/acrylic acid (AAc) particles were fabricated using the same reaction condition as NIP Am particles above. The initial monomer solution was obtained by dissolving NIPAm (1.3 g), BIS (0.10 g), and AAc (0.072 g) in 150 ml water. All particles were purified via dialysis (Spectra/Por 7 dialysis membranes, MWCO 10,000, VWR) against frequent changes of stirring water for 2 weeks at 4° C.

Example 5

Particle Size Dependence on Temperature and pH

Figure 2:
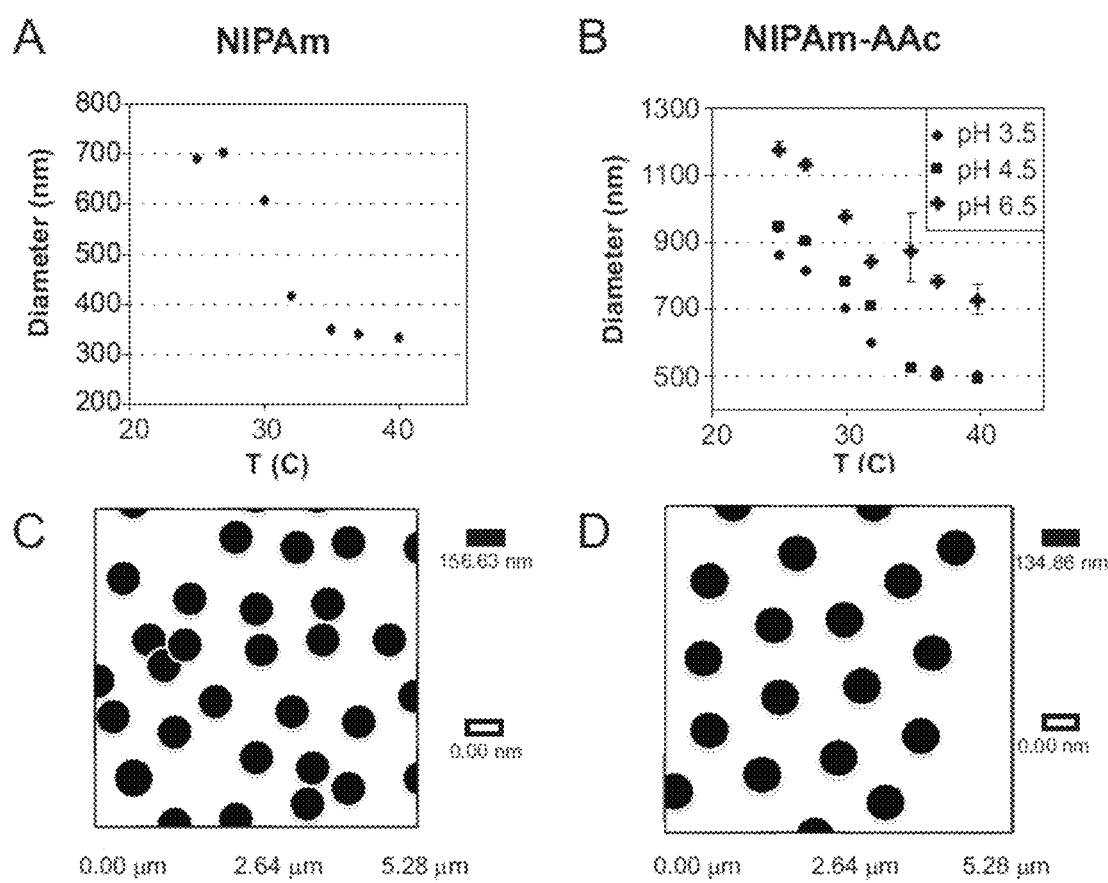
FIG. 2. Particle characterization. (A) Light scattering measurement of NIPAm particle size as a function of temperature (diameter decreases as temperature increases). (B) Plots of correlation of the size of NIPAm/AAc particles with temperature (diameter decreases as temperature increases) and pH (diameter decreases as pH decreases). AFM images of (C) NIPAm particles and (D) NIPAm/AAc particles on mica.

Particle size dependence on temperature and pH were determined via Photon Correlation Spectroscopy (PCS, Submicron Particle Size Analyzer, Beckman Coulter). Average values were calculated for 3 measurements using a 200 second integration time, and the solutions were allowed to thermally equilibrate for 10 minutes before each set of measurements. Measured values were then converted to particle sizes via the Stokes-Einstein relationship (Pecora, *Dynamic Light Scattering: Applications of Photo Correlation Spectroscopy*. Springer: 1985; p 436). NIPAm particle size decreased with increasing temperature (FIG. 2A), which is a distinctive characteristic of thermo responsive hydrogels (Spamacci et al., *J Biomater Sci Polym Ed* 2005, 16, (12), 1557-74; Haruyuki Hiratani, *Macromolecular Bioscience* 2005, 5, (8), 728-733; Nahar et al., *Crit Rev Ther Drug Carrier Syst* 2006, 23, (4), 259-318; Wu et al., *Journal of Controlled Release* 2005, 102, (2), 361-372; Zhang et al., *Biomaterials* 2005, 26, (16), 3299-309; Woo et al., *Pharm Res* 2001, 18, (11), 1600-6). The NIPAm/AAc particles showed a similar temperature dependence with respect to particle size, however they also demonstrated a pH dependent behavior (FIG. 2B). At low pH (3.5) AAc groups are protonated and NIPAm/AAc particle size dependence on temperature is similar to underivatized particles. At higher pH (4.5 and 6.5) AAc groups are partially deprotonated and the average particle size increases, likely due to Coulombic interaction between polymeric chain and osmotic pressure resulting from counter ion ingress in particles (Fernandez-Nieves et al., *Macromolecules* 2000, 33, 2114-2118; Ito et al., *Langmuir* 1999, 15, (12), 4289-4294).

Particles were further characterized by atomic force microscopy (AFM) using an NSCRIPTOR™ DPN® System (NanoInk). Images were acquired under AC mode using a silicon tip with a typical resonance frequency of 300 kHz and a radius smaller than 10 nm. Aliquots of 1% w/v particles (50 µL) were deposited on freshly cleaved mica; samples were incubated for ten minutes in humid atmosphere at room temperature to allow deposition, and then dried under nitrogen flow. AFM images of these particles (FIGS. 2C and 2D) show them to be homogeneous in size, and with particle diameters consistent with those measured with light scattering.

Example 6

Molecular Sieving by Hydrogel Particles

Figure 3:
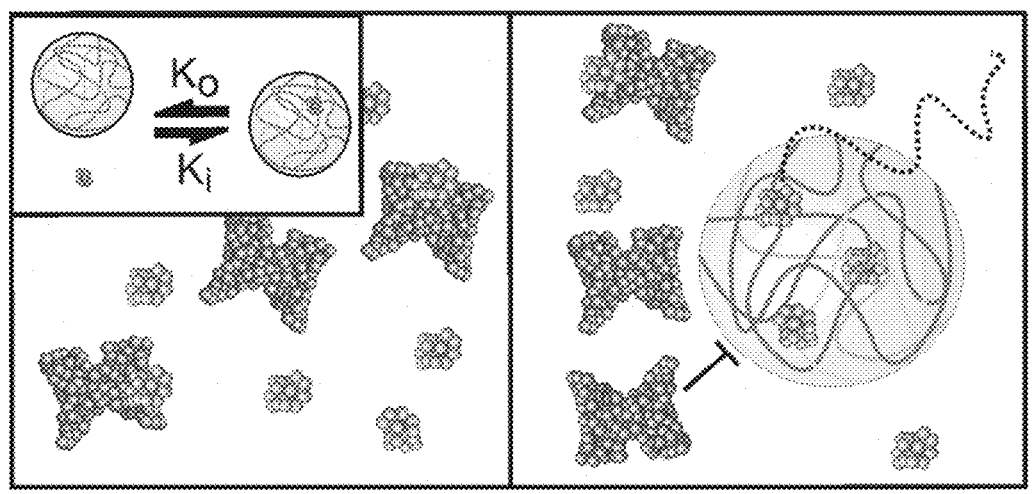
FIG. 3. Schematic drawing of molecular sieving of particles in solution. Low molecular weight proteins are harvested; high molecular weight proteins are excluded.

NIPAm particles were tested for their molecular sieve performance in solution as schematically presented in FIG. 3; the goal being to create particles that could capture proteins and small molecules with molecular weights less than 20,000 Da since the peptidome is thought to contain a rich source of biomarkers (Tirumalai et al., *Molecular & cellular proteomics* 2003, 2, (10), 1096-103; Merrell et al., *Journal of biomolecular techniques* 2004, 15, (4), 238-48; Orvisky et al., *Proteomics* 2006, 6, (9), 2895-902).

This size range contains informative proteins, peptides and metabolites that are difficult, if not impossible, to separate from complex protein mixtures (such as serum or plasma) with adequate yield using 2-D gel electrophoresis or column chromatography. The degree of cross-linking within the particle enabled exclusion of albumin and other high abundance large molecules while capturing molecules with sizes smaller than the cut-off pore size of the particles. Particles with varied degrees of cross-linking were investigated until one was identified that demonstrated an effective 20,000 Da exclusive pore size. These particles were further studied in order to evaluate their sieving efficiency and nonspecific binding of excluded molecules to the particle surface. Because serum albumin is present in large excess (106-109 fold) relative to the proteins and peptides of interest, it was necessary to examine the efficiency and completeness of albumin exclusion.

Figure 4:
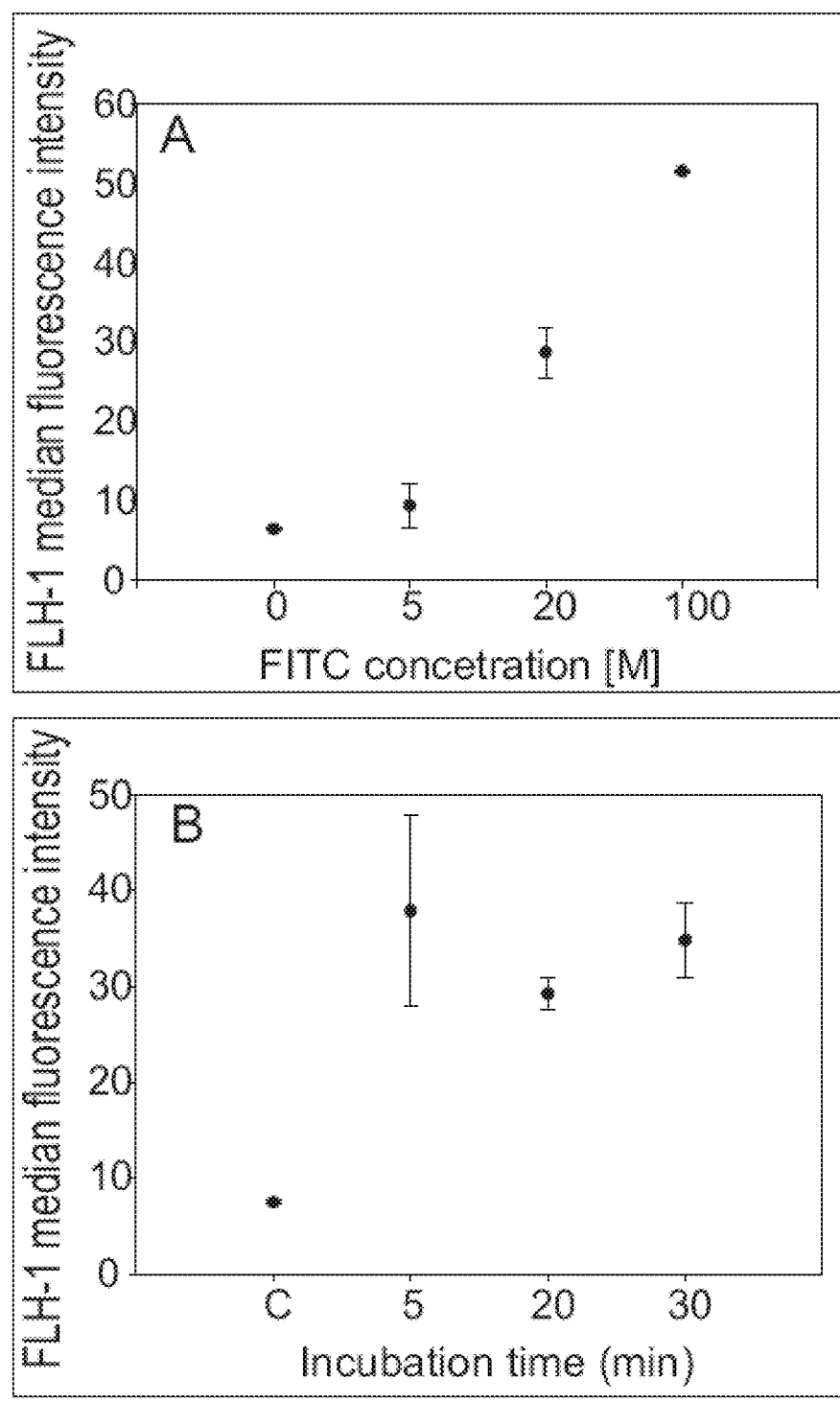
FIG. 4. Flow cytometry analyses of FITC-incubated particles. (A) Uptake is dose dependent. (B) Uptake rapidly reaches saturation with a FITC concentration of 20 µM. NIP Am particles were also incubated with FITC-labeled bovine serum albumin (BSA), MW 66,000 Da, with a dye:molecule ratio of 1:1 (FITC-BSA, Sigma), FITC labeled insulin MW 3,500 Da, with a dye:molecule ratio of 1:7 (Invitrogen), or FITC labeled myoglobin MW 17,000 Da, with a dye:molecule ratio of 1.36. Myoglobin (Sigma) was FITC labeled by means of the HOOK-Dye Labeling Kit (G Bioscience) in accordance of the vendor's instructions. Concentrations of all fluorescent species were adjusted in order to equalize the fluorescence signal.

Two independent methods were used to measure sieving performance: flow cytometry and gel electrophoresis. Aliquots of NIPAm particles (50 µL, 10 mg/mL) were incubated with target molecular species, and centrifuged to collect the particles (7 minutes, 25° C., 16,100 rcf). The supernatant was removed and the particles were resuspended in 1 mL water. Centrifugation and washing were repeated three times and the fluorescent intensity of the particles was measured using a FACScan flow cytometer (Becton Dickinson). The background fluorescent signal of untreated particles in water was used as a reference for all measurements. Fluorescein isothiocyanate (FITC, MW 389 Da) was used as a model to study small molecule uptake and the dependence of uptake on incubation time and concentration. Particles incubated with various concentrations of FITC 5 µM, 20 µM, and 100 µM) showed a dose dependent uptake rate (FIG. 4A) toward saturation. Time course studies demonstrated that FITC uptake could occur rapidly (5 minutes, FIG. 4B) at 10% v/v particles concentration.

Figure 5:
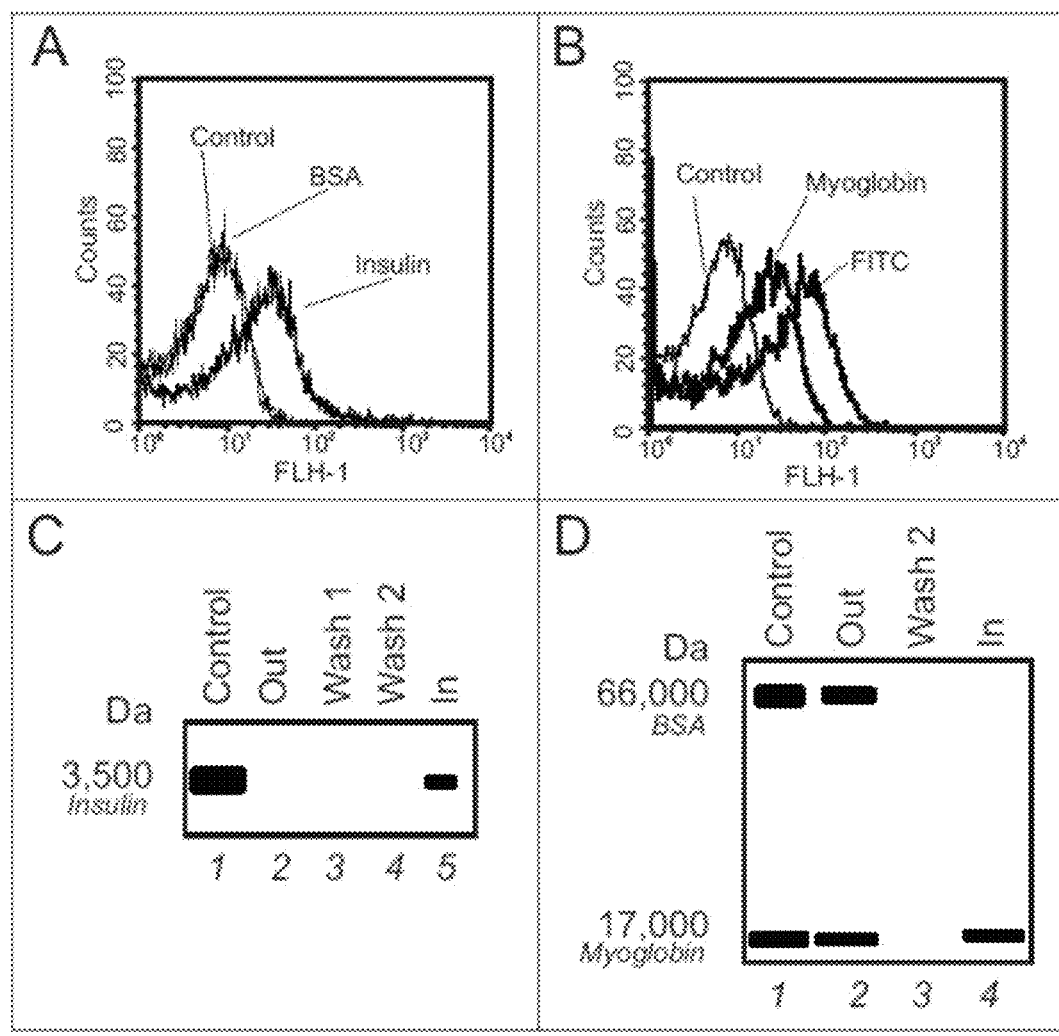
FIG. 5. NIPAm particles incubated with FITC and FITC-labeled proteins: Flow cytometry measurements of (A) BSA and insulin, (B) myoglobin and free FITC. (C) SDS-PAGE of particles incubated with insulin: Lane 1) insulin solution (Control), 2) NIPAm supernatant (Out, substance excluded from the particles), 3) wash 1, 4) wash 2, 5) NIPAm particles (In, substance captured by the particles). (D) SDS-PAGE of NIP Am particles incubated with BSA and myoglobin: 1) BSA and myoglobin (Control), 2) NIPAm supernatant (Out), 3) wash 2, 4) NIPAm particles (In). BSA is totally excluded.

As shown in FIGS. 5A and 5B particles incubated with FITC-BSA (MW 66,000 Da) have no detectable shift in fluorescence signal relative to the particle background fluorescence, which indicates no detectable BSA uptake or non specific binding by the particles. On the other hand, incubation with FITC-insulin (MW 3, SOO Da) results in a right shift in fluorescence relative to the control, confirming the uptake of insulin by the particles. FITC alone (MW 389 Da), a molecule in the size range of many metabolites, and FITC-myoglobin (MW 17,000 Da), another protein below the effective size cut-off of the particles, were both rapidly captured.

These findings were confirmed by SDS-PAGE analysis. The particles were directly loaded on the gel after incubation with protein solution and washing. Insulin (FIG. 5C), and myoglobin (FIG. 5D) were trapped by particles, while BSA was totally excluded (Figure SD).

Example 7

Incorporation of a Charged Bait in the Molecular Sieving Particles Significantly Enhances Uptake Passive molecular sieving cannot effectively harvest and concentrate all of the target proteins in solution because the concentration of the captured target protein in the particles is dependent on the equilibrium between rates of proteins exiting and entering particles and the concentration of the target protein in the bulk solution. Consequently particles were constructed that incorporated an affinity bait to facilitate harvesting of target proteins and prevent the captured proteins from exiting the particle.

Figure 6:
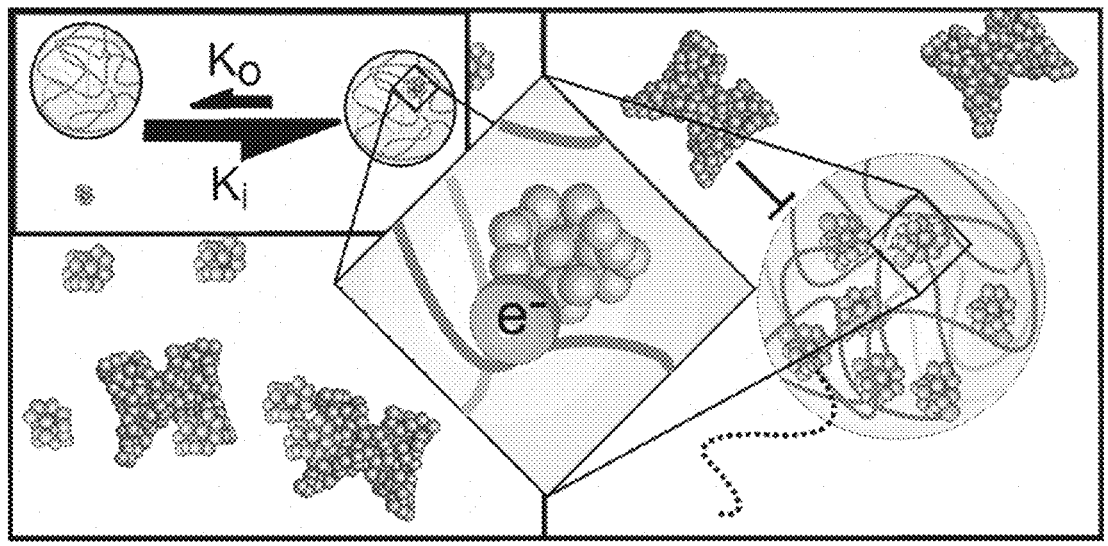
FIG. 6. Schematic depiction of affinity-based sequestering.

A negatively-charged moiety was selected as a bait for proteins and molecules that have a positive net charge. Incorporation of a negatively-charged bait within the particles would allow the particles to preferentially sequester and concentrate positively-charged proteins, peptides and other biomolecules. Therefore, particles were prepared based on a NIPAm/AAc copolymer, which carries a large net negative charge at pH values greater than 3.5. As shown schematically in FIG. 6, the presence of charged bait, in principle, should enhance substantially the Keq and thereby achieve a significantly higher concentration of the target protein inside the particle compared to the solution outside the particle.

Figure 7:
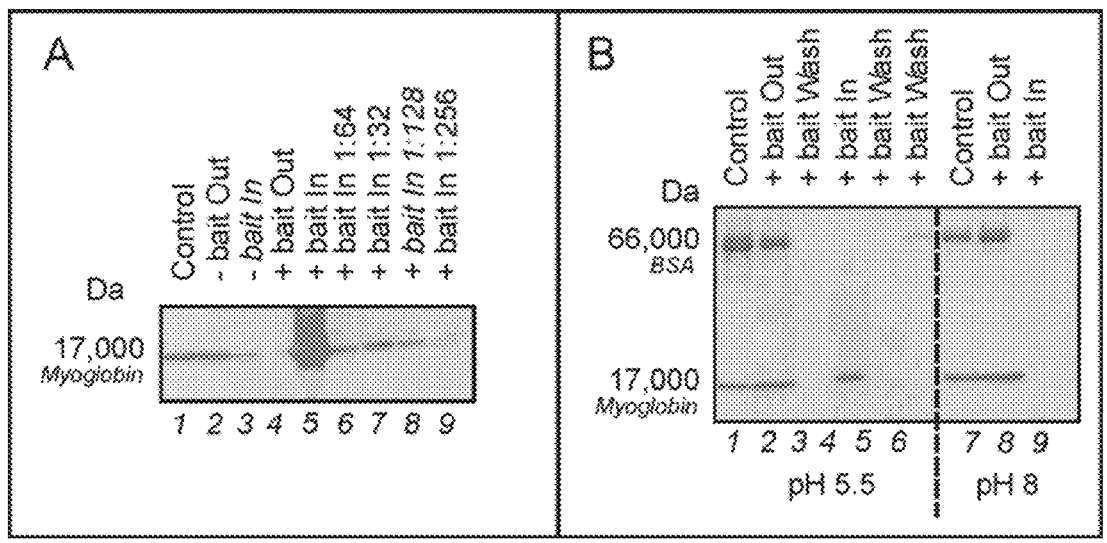
FIG. 7. Protein sequestering by NIPAm/AAc particles (+bait) versus NIPAm particles (−bait), SDS-PAGE analysis of (A) Myoglobin (aqueous solution, pH 5.5) sequestration by particles+ and −bait. Lane 1) myoglobin, 2) NIPAm supernatant (Out), 3) NIPAm particle (In), 4) NIPAm/AAc supernatant (Out), 5) NIPAm/AAc particle (In), 6) NIPAm/AAc particles 1:64, 7) NIPAm/AAc particles 1:32, 8) NIPAm/AAc particles 1:128, and 9) NIPAm/AAc particles 1:256. (B) BSA and myoglobin sequestration by particles+bait (NIPAm/AAc) at two pH values. Lane 1) BSA and myoglobin, pH 5.5, 2) NIPAm/AAc supernatant (Out) pH 5.5, 3) wash 3 pH 5.5, 4) NIPAm/AAc particles (In) pH 5.5, 5) wash 2 pH 5.5, 6) wash 1 pH 5.5, 7) BSA and myoglobin, pH 8, 8) NIPAm/AAc supernatant (Out) pH 8, and 9) NIPAm/AAc particles (In) pH 8.

As shown in FIG. 7 A, NIPAm/AAc particles concentrated analytes from solution with substantially greater efficiency relative to underivatized NIP Am particles. Suspensions of NIPAm and NIPAm/AAc particles (10 mg/mL) were incubated for 1 hour with myoglobin (MW 17,000 Da, 20 µM in water). Following incubation with NIPAm particles, significant levels of myoglobin remained in the bulk solution with some protein being bound by the particles, which lack the anionic affinity bait (FIG. 7 A). Following incubation with NIPAm/AAc particles, which contain the anionic affinity bait, all of the myoglobin had been captured by the NIPAm/AAc particles, with no detectable myoglobin remaining in bulk solution. Correlating myoglobin band intensity for serial dilutions of NIPAm/AAc particles with that of NIP Am particles suggests that the NIPAm/AAc particles sequestered myoglobin with more than 128-fold greater efficiency compared with particles that lack the affinity bait.

In order to demonstrate that the superior protein uptake associated with NIPAm/AAc particles was charge driven, aliquots of a solution containing myoglobin (20 µM) and BSA (20 µM) were incubated with NIPAm/AAc particles in phosphate buffer titrated to either pH 5.5 or pH 8 (FIG. 7B). Particles were separated by centrifugation and washed three times with MilliQ water. At pH 5.5, myoglobin (pI 7) is expected to be positively charged, and electrostatic interactions between the protein and the negatively charged carboxyl groups of NIPAm/AAc particles would be attractive. However at pH 8, myoglobin would be negatively charged, and any electrostatic interactions with the anionic particles would likely be repulsive in nature. Consistent with these expectations, myoglobin was efficiently sequestered by NIPAm/AAc particles at pH 5.5 where the protein and the particles have opposite net charges, and no myoglobin was detectable in particles that had been incubated with myoglobin at pH 8 (FIG. 7B).

Figure 8:
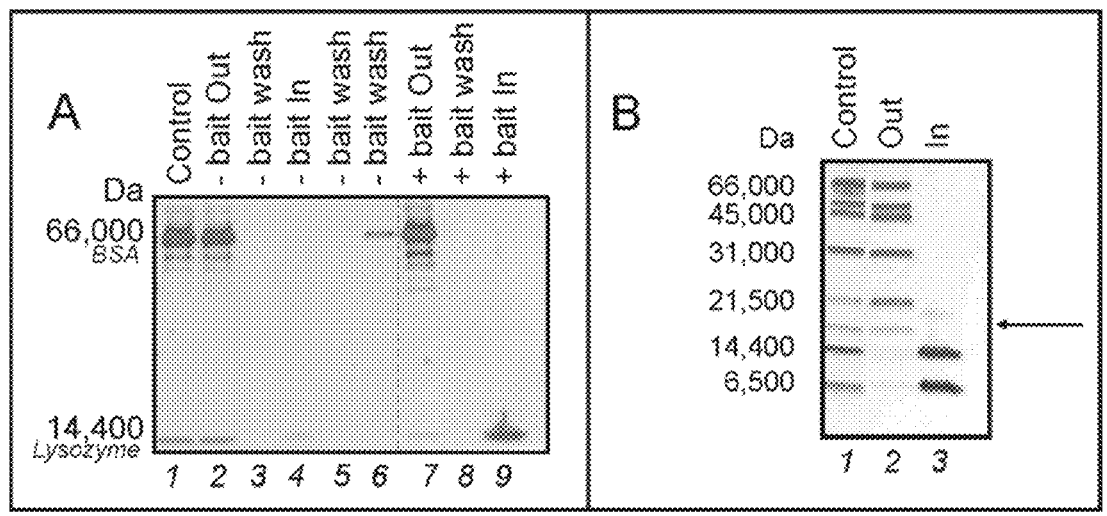
FIG. 8. (A) SDS-PAGE analysis of particles− and +bait incubated with BSA and lysozyme: Lane 1) BSA and lysozyme solution prior to particle introduction, 2) NIP Am (−bait) supernatant (Out), 3) wash 3, 4) NIPAm (−bait) particles (In), 5) wash 2, 6) wash 1, 7) NIPAm/AAc (+bait) supernatant (Out), 8) wash 3, and 9) NIPAm/AAc (+bait) particles (In). (B) SDS-PAGE analysis of NIPAm/AAc particles (+bait) incubated with molecular weight (MW) markers: 1) MW markers, 2) NIPAm/AAc supernatant (Out), and 3) NIPAm/AAc particles (In).

The efficiency of NIPAm/AAc affinity baited particles to bind and concentrate proteins and peptides with MW less than ca. 20,000 Da is illustrated in FIG. 8A. NIPAm/AAc and NIP Am particles were each incubated for 1 hour with lysozyme (20 µM) and BSA (20 µM) in Tris (pH 7.50 mM). The particles then were washed with three 1 mL volumes of water, and the captured proteins were electro-eluted onto an SDS polyacrylamide gel.

While the NIPAm/AAc particles appeared to have captured all of the lysozyme present in the solution, there was no indication that BSA had been bound non-specifically by the particles. As was observed with myoglobin, NIP Am particles, lacking the affinity bait, did not appear to significantly concentrate lysozyme.

Figure 9:
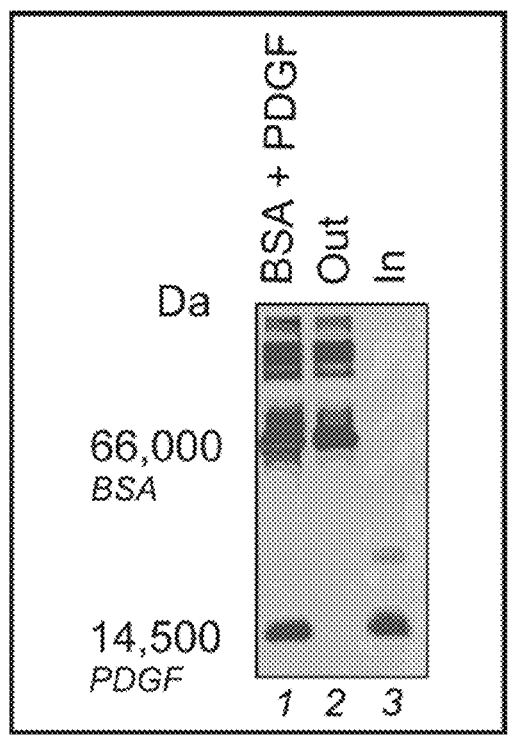
FIG. 9. SDS PAGE analysis of particles+bait incubated with PDGF Band BSA. Lane 1) BSA and PDGF B, 2) NIPAm/AAc supernatant (Out), 3) NIPAm/AAc particles (In).

A solution of protein molecular weight markers was used to further assess the molecular weight cut off (MWCO) of the proteins sequestered by the particles (FIG. 8B). The solution consisted of 0.5 mg/mL of each of the following proteins: aprotinin (MW 6,500 Da, Sigma-Aldrich), lysozyme (MW 14,400 Da, Sigma-Aldrich), trypsin inhibitor (MW 21,500 Da, Invitrogen), carbonic anhydrase (MW 31,000 Da, SigmaAldrich), ovalbumin (MW 45,000 Da, Sigma-Aldrich), and BSA (MW 66,000 Da, Fisher Scientific) dissolved in Tris (PH 7, 50 mM). It was found that NIPAm/AAc baited particles, incubated with the protein solution, effectively captured and concentrated all protein molecules with MW less than ca. 21,500 Da, and did not bind any proteins with MW greater than 21,500 Da. NIP Am particles showed a similar MWCO with MW 14,400 Da or smaller and not binding proteins MW>=14,400 Da. The MWCO resolution achieved with NIPAm/AAc and NIP Am particles compares favorably, or exceeds, that associated with standard molecular sieving chromatography 41. In order to further determine the molecular sieving properties of the beads, NIPAm/AAc particles were incubated with platelet derived growth factor B (0.003 mg/mL, 14,500 Da, Cell Signaling) and BSA (0.067 mg/mL) in Tris (100 mM pH 7) for one hour. Washing procedure was the same as described before. SDS PAGE in FIG. 9 shows complete PDGF uptake and BSA exclusion. PDGF is a representative model for low abundance low molecular weight protein present in the blood and PDGF-B concentration in blood is 3.3 ng/mL (Eppley et al., *Plastic and reconstructive surgery* 2004, 114, (6), 1502-842). Because of the drastic change in size particles undergo when the temperature of solution is altered, temperature effects on MWCO were investigated. The solution of molecular weight markers described above was incubated with NIPAm/AAc particles at 25, 37, and 45° C. and the temperature was a factor that did not affect the MWCO (data not shown).

Example 8

Sequestration from Serum

Figure 10:
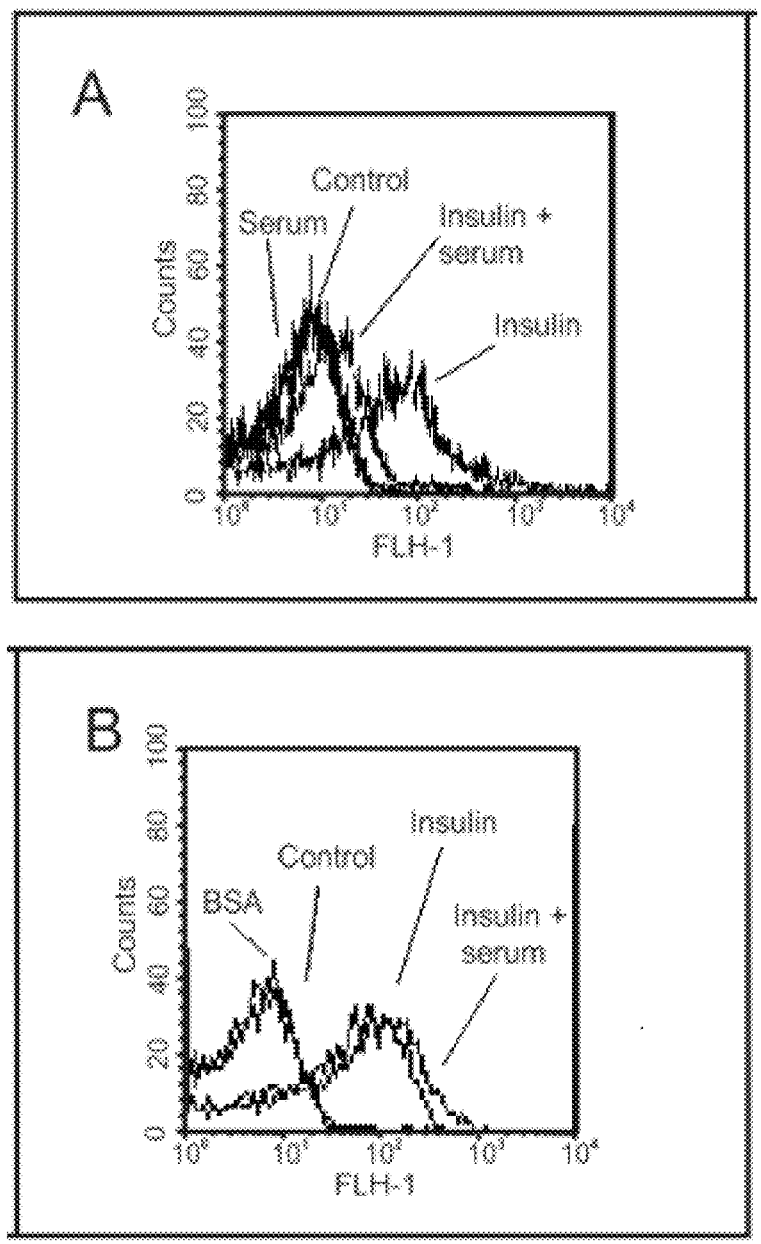
FIG. 10. Flow cytometry analysis of (A) NIPAm and (B) NIPAm/AAc particles incubated with FITe-labeled insulin aqueous solution and FITe-labeled insulin spiked in serum, respectively.

Based on the above results, the ability of the particles to capture small molecules spiked in complex solutions such as serum was then tested to mimic real-world biomarker discovery and analysis type experiments. Aliquots of FITC-labeled insulin (final concentration 40 M) in 1:10 diluted serum were incubated with NIPAm and NIPAm/AAc particles. Flow cytometry analysis demonstrated that NIP Am particles incubated in serum containing FITC-insulin yielded a right shift in fluorescence intensity relative to control particles and particles incubated with serum alone (FIG. 10A).

This result clearly demonstrated the ability of NIP Am particles to capture insulin from a complex matrix such as serum. However, the capture efficiency of the NIPAm particles incubated with a simple aqueous solution containing only insulin was lower than that attained with serum incubated NIP Am particles. While the two classes of particles exhibited a similar uptake of insulin in an aqueous solution, the particles with the charged bait were more efficient in capturing insulin spiked into serum compared to the underivatized particles. (Figure lOB).

Figure 11:
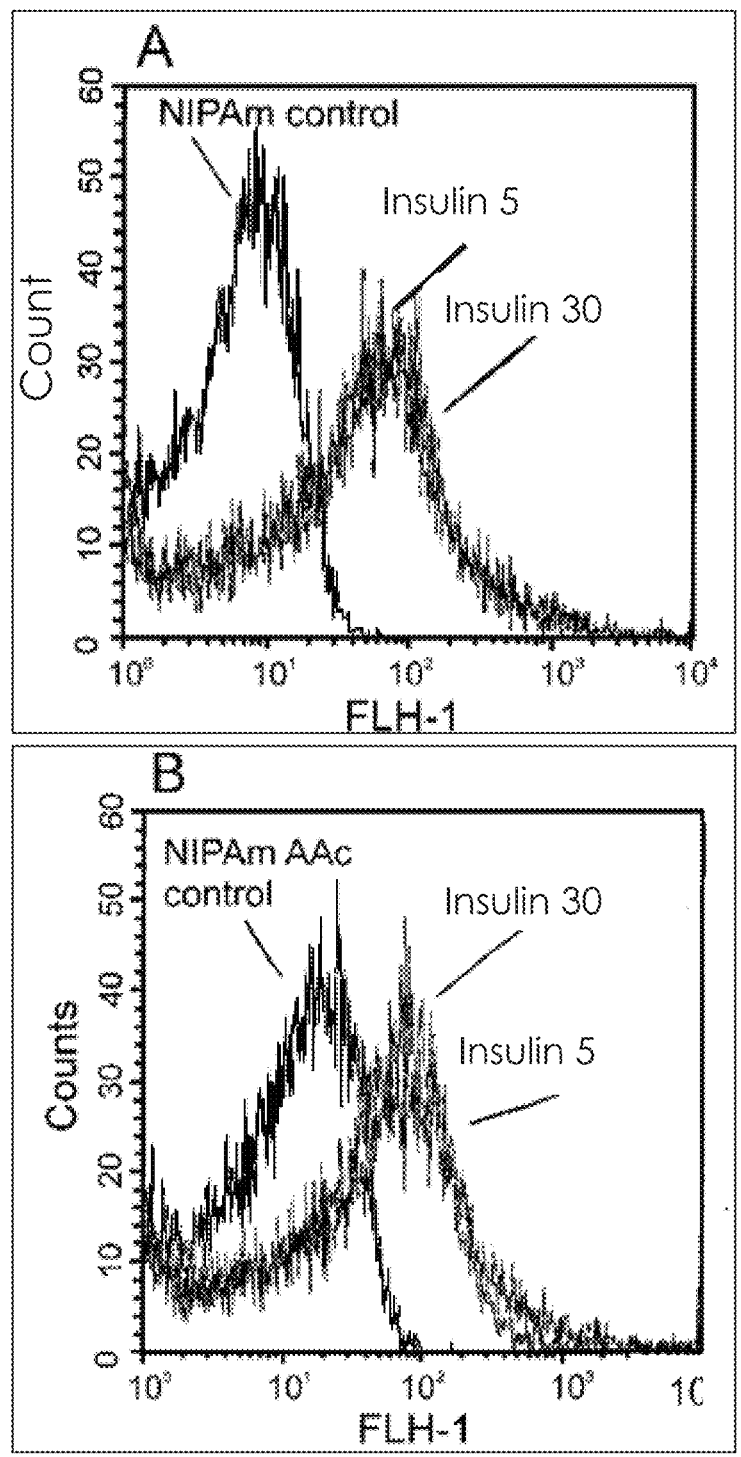
FIG. 11. Flow cytometry time course studies of (A) NIP Am and (B) NIPAm/AAc particles incubated with FITe-labeled insulin.

Time courses uptake studies for NIP Am and NIPAm/AAc particles incubated with FITC-labeled insulin (pI 5.3) were conducted in order to confirm and extend the data obtained for the small molecule, FITe. Histograms of fluorescence intensity associated with Flow cytometry analyses of NIP Am and NIPAm/AAc particles incubated with FITe-labeled insulin collected at different time intervals are reported in FIG. 11. This data indicates that sequestration occurs rapidly (5 minutes) and constant over time.

Example 9

Rapid Time Course of Target Protein Uptake by Bait Containing Particles

In order to prove that the kinetics of protein uptake is very rapid, the amount of protein remaining in bulk solution after incubation with NIPAm/AAc particles was measured by Reverse Phase Protein Arrays (RPPA) (Gulmann et al., *The Journal of pathology* 2006, 208, (5), 595-606). RPPA was chosen as a means to determine protein concentration in particles supernatant since other methods like Bradford assays do not have sufficient sensitivity and our goal was demonstrate how complete the protein removal from bulk solution was. Different amounts of NIPAm/AAc particles (1.15 and 11.5 million) were incubated with lysozyme (20 µM) in Tris (pH 7, 50 mM) in a total volume of 100 µL for periods of 1 and 10 minutes. After centrifugation of the particles, aliquots of supernatant were spotted on a nitrocellulose coated slide (FAST slide, Whatman) using an Aushon 2470 robotic arrayer (Aushon Biosystems). Arrays were stained with a colloidal gold solution, AuroDye Forte Kit (Amersham), images were acquired using a PowerLook 1120 scanner (Umax), and numeric values were obtained from images with ImageQuant (GE Healthcare) and processed with SigmaPlot (Systat). The bulk solution after a one minute incubation with 1.15 million particles contained 28% of the initial protein amount, and 15% after ten minutes. Moreover, the solution recovered from incubation with 11.5 million particles after 1 and 10 minutes contained 5% and 9% of the initial amount, respectively (FIG. 12A). It should be noted that, since in all the time course experiments the separation of particles from solution was obtained by centrifugation, reported time values refer to incubations time intervals only. Beyond that particles were in contact with solution for additional 7 minutes required for centrifugation.

The kinetics of protein uptake by NIPAm/AAc particles was further investigated by incubating particles with BSA (20 µM) and lysozyme (20 µM) in Tris (pH 7, 50 mM) at room temperature and using SDS-PAGE to monitor lysozyme uptake at time points of 1, 10, 20, 30, and 60 minutes (FIG. 12B). The results of this experiment showed that lysozyme sequestration was nearly complete after 1 minute and was complete by 60 minutes, confirming that the process occurs very quickly as indicated in the flow cytometry time course study described above. As expected, BSA was excluded by the particles, and none of the BSA was taken-up by the NIPAm/AAc throughout the duration of the experiment (60 minutes).

Example 10

Demonstration of Isolation and Enrichment of Low Molecular Weight and Low Abundance Analytes from Serum The ability of NIP AM and NIPAm/AAc particles to sequester and concentrate low concentration candidate protein biomarkers from serum for proteomic analysis was evaluated by incubating the particles with a 1:10 v Iv dilution of serum in water for 1 hour. The trapped proteins were electrophoretically eluted from the particles under denaturing conditions and then trypsin digested. The particles were heated in SDS sample buffer for 5 minutes at 100° C. and loaded on a 4-20% Tris Glicine gel (Invitrogen). Bands below 30 kDa were cut and in-gel trypsin digestion was performed (Camerini et al., *Proteomics Clin. Appl.* 2007, 1, 176-184). The resulting peptide fragments were analyzed by online liquid chromatography/electrospray ionization tandem mass spectrometry (LC/ESI MS) using LTQ-Orbitrap mass spectrometer (Thermo Fisher). Reverse phase column was slurry-packed in-house with 5 m, 20 A pore size C18 resin (Michrom BioResources, CA) in 100 mm i.d.×10 cm long fused silica capillary (Polymicro Technologies, Phoenix, Ariz.) with a laser-pulled tip. After sample injection, the column was washed for 5 minutes with mobile phase A (0.1% formic acid) and peptides were eluted using a linear gradient of 0% mobile phase B (0.1% formic acid, 80% acetonitrile) to 50% mobile phase B in 50 minutes at 200 nl/min, then to 100% B in an additional 5 minutes. The L TQ mass spectrometer was operated in a data-dependent mode in which each full MS scan was followed by five MS/MS scans were the five most abundant molecular ions were dynamically selected and fragmented by collision-induced dissociation (CID) using a normalized collision energy of 35%. MS/MS data were matched against the NCB I (National Center for Biotechnology Information) human protein database with the program SEQUEST (Bioworks software, Thermo) using full tryptic cleavage constraints. High-confidence peptide identifications were obtained by applying the following filters to the search results: cross-correlation score (XCorr)>=1.9 for 1+, 2.2 for 2+, 3.5 for 3+, and a maximum probability for a random identification of 0.01. The list of identified proteins in Table 1 and Table 2 demonstrated that albumin and other high abundance serum proteins were not present in the particles. On the other hand, the list of identified proteins indicates that the particles sequestered rare and small-sized serum proteins and peptides.

TABLE 1

| Reference | Accession | P (pep) | Sf | Score | MW |
|---|---|---|---|---|---|
| complement component 1, q subcomponent, gamma polypeptide [*Homo sapiens*] | 56786155.0 | 4.83E−12 | 3.43E+00 | 40.28 | 25757.13 |
| complement component 1, r subcomponent [*Homo sapiens*] | 66347875.0 | 5.65E−12 | 2.72E+00 | 30.24 | 80147.95 |
| haptoglobin-related protein [*Homo sapiens*] | 45580723.0 | 1.12E−11 | 9.76E−01 | 10.22 | 39004.70 |
| PREDICTED: similar to Putative S100 calcium-binding protein A11 pseudogene [*Homo sapiens*] | 113419208.0 | 1.12E−11 | 9.80E−01 | 10.22 | 11254.79 |
| complement component 4A preproprotein [*Homo sapiens*] | 67190748.0 | 1.12E−11 | 3.58E+00 | 40.24 | 192663.60 |

TABLE 1-continued

| Reference | Accession | P (pep) | Sf | Score | MW |
|---|---|---|---|---|---|
| orosomucoid 1 precursor [Homo sapiens] | 9257232.0 | 1.12E−11 | 8.17E−01 | 10.13 | 23496.77 |
| CD5 antigen-like (scavenger receptor cysteine rich family) [Homo sapiens] | 5174411.0 | 1.12E−11 | 3.80E+00 | 40.25 | 38062.96 |
| serum amyloid P component precursor [Homo sapiens] | 4502133.0 | 1.12E−11 | 4.15E+00 | 50.20 | 25371.13 |
| complement component 1, q subcomponent, B chain precursor [Homo sapiens] | 87298828.0 | 1.12E−11 | 9.82E−01 | 10.26 | 26704.49 |
| apolipoprotein A-I preproprotein [Homo sapiens] | 4557321.0 | 1.12E−11 | 6.86E−01 | 10.12 | 30758.94 |
| haptoglobin [Homo sapiens] | 4826762.0 | 1.12E−11 | 3.70E+00 | 40.21 | 45176.59 |
| complement component 1, q subcomponent, A chain precursor [Homo sapiens] | 7705753.0 | 1.12E−11 | 8.24E−01 | 10.15 | 26000.19 |
| platelet factor 4 (chemokine (C-X-C motif) ligand 4) [Homo sapiens] | 4505733.0 | 1.12E−11 | 1.80E+00 | 20.16 | 10837.89 |
| immunoglobulin J chain [Homo sapiens] | 21489959.0 | 1.12E−11 | 9.45E−01 | 10.15 | 18087.00 |
| lysozyme precursor [Homo sapiens] | 4557894.0 | 1.12E−11 | 9.03E−01 | 10.15 | 16526.29 |
| transthyretin [Homo sapiens] | 4507725.0 | 1.12E−11 | 6.77E−01 | 10.13 | 15877.05 |
| dermcidin preproprotein [Homo sapiens] | 16751921.0 | 1.12E−11 | 8.66E−01 | 10.13 | 11276.83 |
| mesotrypsin preproprotein [Homo sapiens] | 21536452.0 | 1.12E−11 | 9.37E−01 | 10.17 | 26680.18 |
| alpha 1 globin [Homo sapiens] | 4504347.0 | 1.12E−11 | 9.62E−01 | 10.16 | 15247.92 |
| beta globin [Homo sapiens] | 4504349.0 | 1.12E−11 | 9.36E−01 | 10.17 | 15988.29 |
| hypothetical protein LOC649897 [Homo sapiens] | 91206438.0 | 1.12E−11 | 8.68E−01 | 10.18 | 22058.92 |
| complement component 1, s subcomponent [Homo sapiens] | 41393602.0 | 1.12E−11 | 9.25E−01 | 10.15 | 76634.85 |
| protein kinase C and casein kinase substrate in neurons 2 [Homo sapiens] | 6005826.0 | 1.12E−11 | 8.23E−01 | 10.15 | 55870.13 |
| PREDICTED: similar to Keratin, type II cytoskeletal 2 oral (Cytokeratin-2P) (K2P) (CK 2P) [Homo sapiens] | 89036176.0 | 1.12E−11 | 8.89E−01 | 10.14 | 36406.56 |
| platelet factor 4 variant 1 [Homo sapiens] | 4505735.0 | 1.12E−11 | 8.70E−01 | 10.19 | 11545.28 |
| bromodomain containing 7 [Homo sapiens] | 41350212.0 | 1.12E−11 | 8.63E−01 | 10.18 | 74092.27 |
| SH3-domain binding protein 2 [Homo sapiens] | 19923155.0 | 1.12E−11 | 2.64E−01 | 10.13 | 62220.29 |
| zinc finger, CCHC domain containing 11 isoform c [Homo sapiens] | 57863250.0 | 1.12E−11 | 8.14E−01 | 10.17 | 184587.10 |
| apolipoprotein A-II preproprotein [Homo sapiens] | 4502149.0 | 1.12E−11 | 8.90E−01 | 10.14 | 11167.90 |
| heterogeneous nuclear ribonucleoprotein D isoform d [Homo sapiens] | 51477708.0 | 1.12E−11 | 6.31E−01 | 10.18 | 30653.14 |
| polo-like kinase 4 [Homo sapiens] | 21361433.0 | 1.12E−11 | 6.16E−01 | 10.13 | 109016.40 |
| apolipoprotein L1 isoform a precursor [Homo sapiens] | 21735614.0 | 1.12E−11 | 6.63E−01 | 10.12 | 43946.95 |
| coronin, actin binding protein, 2A [Homo sapiens] | 16554583.0 | 1.12E−11 | 9.33E−01 | 20.14 | 59697.38 |

Table 1. Mass spectrometry analysis of proteins electro-eluted from NIPAm particles after 1 hr incubation with 1:10 v Iv dilution serum, P(pep) displays the probability value for the peptide, Sf displays the final score that indicated how good the protein match is, Score displays a value that is based upon the probability that the peptide is a random match to the spectral data, Accession displays a unique protein identification number for the sequence.

TABLE 2

| Reference | Accession | P (pep) | Sf | Score | MW |
|---|---|---|---|---|---|
| complement component 1, q subcomponent, gamma polypeptide [Homo sapiens] | 56786155.0 | 3.55E−14 | 1.86E+00 | 20.30 | 25757.13 |
| hypothetical protein LOC649897 [Homo sapiens] | 91206438.0 | 3.55E−14 | 2.90E+00 | 30.26 | 22058.92 |
| PREDICTED: similar to Putative S100 calcium-binding protein A11 pseudogene [Homo sapiens] | 113419208.0 | 3.55E−14 | 1.46E+00 | 20.25 | 11254.79 |
| apolipoprotein C-III precursor [Homo sapiens] | 4557323.0 | 3.55E−14 | 9.79E−01 | 10.24 | 10845.50 |
| pro-platelet basic protein precursor [Homo sapiens] | 4505981.0 | 3.55E−14 | 5.61E+00 | 60.25 | 13885.42 |
| complement component 3 precursor [Homo sapiens] | 4557385.0 | 3.55E−14 | 9.80E−01 | 10.20 | 187045.30 |
| small nuclear ribonucleoprotein polypeptide E [Homo sapiens] | 4507129.0 | 3.55E−14 | 9.15E−01 | 10.19 | 10796.64 |
| keratin 2 [Homo sapiens] | 47132620.0 | 3.55E−14 | 5.75E+00 | 70.21 | 65393.19 |
| albumin precursor [Homo sapiens] | 4502027.0 | 3.55E−14 | 9.28E+00 | 100.22 | 69321.63 |
| ribosomal protein L37a [Homo sapiens] | 4506643.0 | 3.55E−14 | 9.73E−01 | 10.21 | 10268.48 |
| complement component 4A preproprotein [Homo sapiens] | 67190748.0 | 3.55E−14 | 1.91E+00 | 20.17 | 192663.60 |
| A-gamma globin [Homo sapiens] | 28302131.0 | 3.55E−14 | 9.44E−01 | 10.14 | 16118.27 |
| platelet factor 4 (chemokine (C-X-C motif) ligand 4) [Homo sapiens] | 4505733.0 | 3.55E−14 | 3.44E+00 | 40.18 | 10837.89 |
| PREDICTED: hypothetical protein [Homo sapiens] | 113418327.0 | 3.55E−14 | 8.55E−01 | 10.19 | 31688.42 |
| H4 histone family, member J [Homo sapiens] | 4504315.0 | 3.55E−14 | 1.51E+00 | 20.13 | 11360.38 |
| lysozyme precursor [Homo sapiens] | 4557894.0 | 3.55E−14 | 9.66E−01 | 10.20 | 16526.29 |
| mesotrypsin preproprotein [Homo sapiens] | 21536452.0 | 3.55E−14 | 9.68E−01 | 10.18 | 26680.18 |
| alpha 1 globin [Homo sapiens] | 4504347.0 | 3.55E−14 | 9.15E−01 | 10.14 | 15247.92 |
| fibrinogen, alpha polypeptide isoform alpha-E preproprotein [Homo sapiens] | 4503689.0 | 3.55E−14 | 8.35E−01 | 10.12 | 94914.27 |
| hypothetical protein LOC55683 [Homo sapiens] | 21361734.0 | 3.55E−14 | 6.53E−01 | 10.12 | 83244.77 |
| crumbs homolog 1 precursor [Homo sapiens] | 41327708.0 | 3.55E−14 | 6.87E−01 | 10.15 | 154080.40 |
| PREDICTED: similar to glutamate receptor, ionotropic, N-methyl D-aspartate-like 1A isoform 1 isoform 1 [Homo sapiens] | 41146739.0 | 3.55E−14 | 6.26E−01 | 10.15 | 41686.95 |
| PREDICTED: similar to Neutrophil defensin 1 precursor (HNP-1) (HP-1) (HP1) (Defensin, alpha 1) [Homo sapiens] | 113419903.0 | 3.55E−14 | 7.75E−01 | 10.12 | 10194.18 |
| CDK5 regulatory subunit associated protein 1 isoform b [Homo sapiens] | 28872784.0 | 3.55E−14 | 9.05E−01 | 10.12 | 56187.84 |
| complement component 1, q subcomponent, B chain precursor [Homo sapiens] | 87298828.0 | 3.55E−14 | 8.90E−01 | 10.15 | 26704.49 |
| interferon-induced protein with tetratricopeptide repeats 3 [Homo sapiens] | 31542980.0 | 3.55E−14 | 9.40E−01 | 10.22 | 55949.57 |
| lamin A/C isoform 1 precursor [Homo sapiens] | 27436946.0 | 3.55E−14 | 8.73E−01 | 10.14 | 74094.81 |
| double C2-like domains, beta [Homo sapiens] | 6005997.0 | 3.55E−14 | 5.53E−01 | 10.13 | 45920.53 |
| desmoglein 4 [Homo sapiens] | 29789445.0 | 3.55E−14 | 9.06E−01 | 10.13 | 113751.30 |

TABLE 2-continued

| Reference | Accession | P (pep) | Sf | Score | MW |
|---|---|---|---|---|---|
| cadherin EGF LAG seven-pass G-type receptor 1 [Homo sapiens] | 7656967.0 | 3.55E–14 | 1.56E+00 | 20.14 | 329276.70 |
| procollagen, type III, alpha 1 [Homo sapiens] | 4502951.0 | 3.55E–14 | 9.12E–01 | 10.15 | 138470.20 |
| ATPase, H+ transporting, lysosomal 14 kD, V1 subunit F [Homo sapiens] | 20357547.0 | 3.55E–14 | 8.61E–01 | 10.16 | 13361.95 |

Table 2. Mass spectrometry analysis of proteins electroeluted from NIPAmJAAc particles after 1 hr incubation with 1:10 v Iv dilution serum, P(pep) displays the probability value for the peptide, Sf displays the final score that indicated how good the protein match is, Score displays a value that is based upon the probability that the peptide is a random match to the spectral data, Accession displays a unique protein identification number for the sequence.

Example 11

Protein Sequestration by Particle Blocks Protease Degradation

Figure 13:
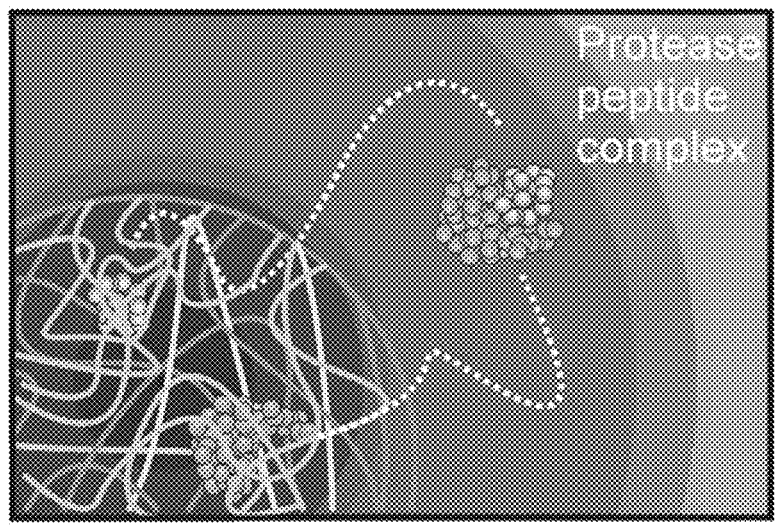
FIG. 13. Schematic drawing illustrating the ability of particles to protect proteins from enzymatic degradation.

One of the major problems associated with biological fluids is the potential for sample degradation during collection, transport, storage and analysis. Endogenous clotting cascade enzymes, enzymes released from damaged cells, or exogenous enzymes (from contaminating bacteria) can contribute to the degradation of diagnostically important proteins, as schematically shown in FIG. 13.

Figure 12:
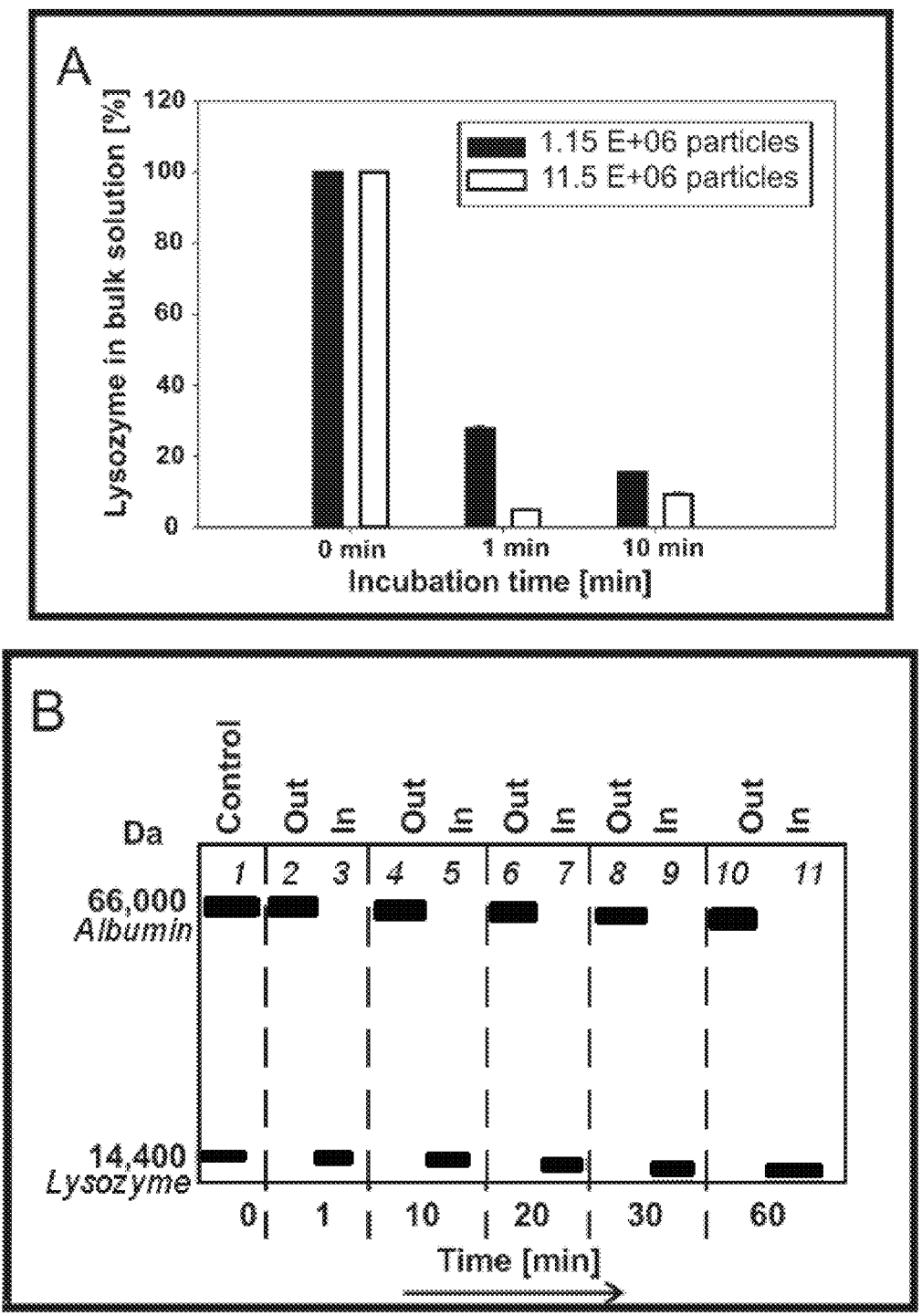
FIG. 12. Uptake time course study (A) Mean values of the percentage, relative to the initial amount, of lysozyme in solution incubated with two quantities of NIPAm/AAc particles as measured by RPPAs (three replicate analyses and standard deviation shown). (B) SDS-PAGE analysis of a lysozyme and BSA solution incubated with NIPAm/AAc particles. Lane 1) BSA and lysozyme solution. 2-11) alternating supernatant (Out) and particles (In) for each of 5, 10, 20, 30, and 60 minutes incubation times. Lysozyme uptake is rapid and complete, while BSA exclusion is total.
Figure 14:
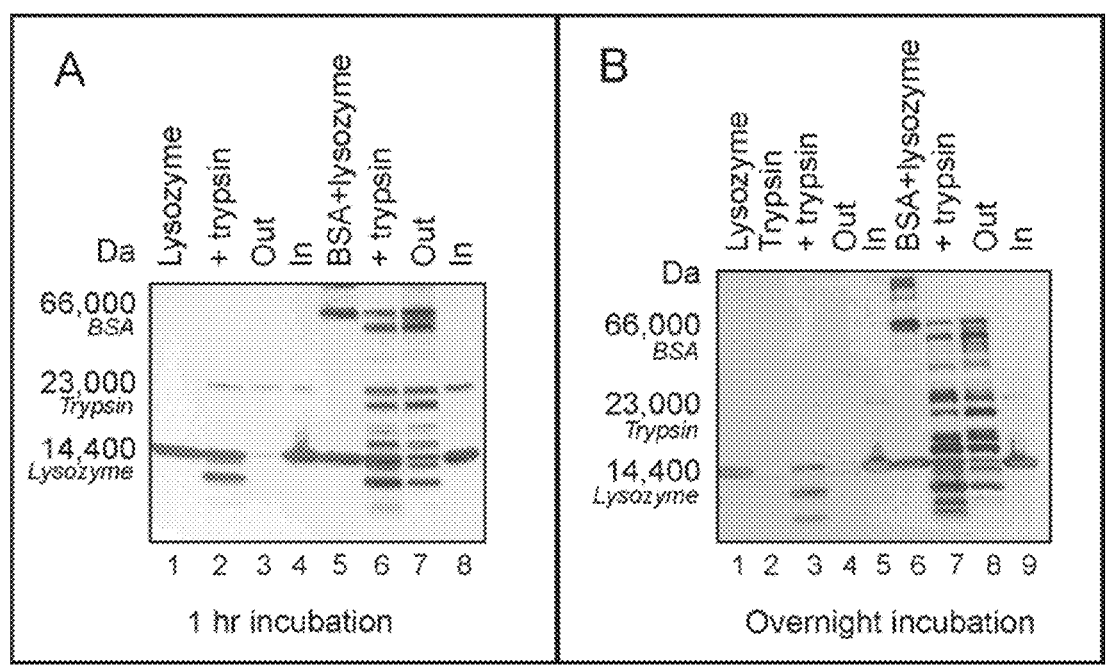
FIG. 14. NIPAm/AAc particles (+bait) protect bound proteins from degradation by enzymes that may be present. (A) NIPAm/AAc particles incubated with a solution containing lysozyme and trypsin for 1 hr: Lane 1) lysozyme, 2) lysozyme incubated with trypsin, 3) NIPAm/AAc supernatant (Out), 4) NIPAm/AAc particles (In), 5) BSA and lysozyme, 6) BSA and lysozyme+protease, 7) NIPAm/AAc particles supernatant (Out), and 8) NIPAm/AAc particles (In). (B) NIPAm/AAc particles incubated overnight with BSA, lysozyme, and trypsin: Lane 1) lysozyme, 2) trypsin, 3) lysozyme+trypsin, 4) NIPAm/AAc supernatant (Out), 5) NIPAm/AAc particles (In), 6) lysozyme and BSA, 7) BSA and lysozyme+protease, 8) NIPAm/AAc supernatant (Out), and 9) NIPAm/AAc particles (In).

The lack of standardized preservation methods could result in bias in high-throughput analysis of serum and plasma (Ayache et al., *American journal of clinical pathology* 2006, 126, (2), 174-84). While it was expected that proteases with MW greater than the MWCO of the particles (~20,000 Da) would be excluded from the interior space of the particles and thereby denied access to captured proteins, smaller proteases such as trypsin (23,800 Da) are more likely to be able to enter the particles. Additionally, it was not known whether proteases that entered charged-bait particles would retain their enzymatic potency when both the substrate proteins and the enzyme were sequestered by the particles (FIG. 12). Therefore, NIPAm/AAc particles were incubated at 37° C. in a pH 7 NH4HC03 (100 mM) solution containing lysozyme (0.5 mg/mL) and trypsin (0.05 mg/mL, Promega). Trypsin was selected for these studies based on its small size and the fact that the tryptic digestion of lysozyme would produce very characteristic cleavage products. The conditions used in this experiment would allow both lysozyme and trypsin to enter the particle. Analysis of the captured proteins by SDS PAGE after incubation for 1 hour and overnight showed only two bands—one corresponding to trypsin and the other to the full length lysozyme, indicating that no degradation of the protein had occurred (FIG. 14A). Incubation of lysozyme (0.5 mg/mL) with trypsin (0.05 mg/mL) at 37° C. in a pH 7 NH4HC03 (100 mM) solution in the absence of NIPAm/AAc particles resulted in degradation of lysozyme. SDS-PAGE analysis of the reaction after incubation for 1 hour and overnight clearly indicated the presence of low molecular weight peptide fragments, which showed that lysozyme was proteolyzed by trypsin in the absence of NIPAm/AAc particles. These results clearly indicate that sequestration of small proteins by affinity-bait particles can effectively shield bound proteins from proteases including those that are capable of entering the particles interior.

In order to better understand the benefits associated with sequestration of proteins by NIPAm/AAc affinity-bait particles, NIPAm/AAc particles were incubated at 37° C. with a combination of BSA (0.5 mg/mL), lysozyme (0.5 mg/mL) and trypsin (0.05 mg/mL) in 100 mM NH4HC03 (PH7). As with the previous protection study, the reaction was analyzed using SDS-PAGE after incubating 1 hr and overnight. In the absence of NIPAm/AAc particles, the majority of BSA had been digested after 1 hr and the band corresponding to full-length BSA had disappeared after incubating overnight (FIG. 14B). As was noted earlier, the NIPAm/AAc particles efficiently sequestered both lysozyme and trypsin, and protected lysozyme from proteolysis by trypsin. However, the particles did not bind BSA, and the presence of low molecular weight bands in the supernatant after 1 hour and overnight incubation accompanied by the decrease in intensity of the band corresponding to full-length BSA indicates that BSA was not protected from degradation by trypsin. Suppression of proteolytic activity by enzymes small enough to enter the particles, such as trypsin, may occur because immobilization of the enzymes by the charge-bait particle prevents them from binding substrate proteins or may be the result of steric hindrance associated with trapping of the substrate by the affinity-bait groups in the particle thus preventing enzymes from productively binding target proteins inside the particle. Thus, the functional state of the proteins sequestered by the charge-bait may be similar to that of proteins arrested using a precipitating fixative treatment.

Figure 15:
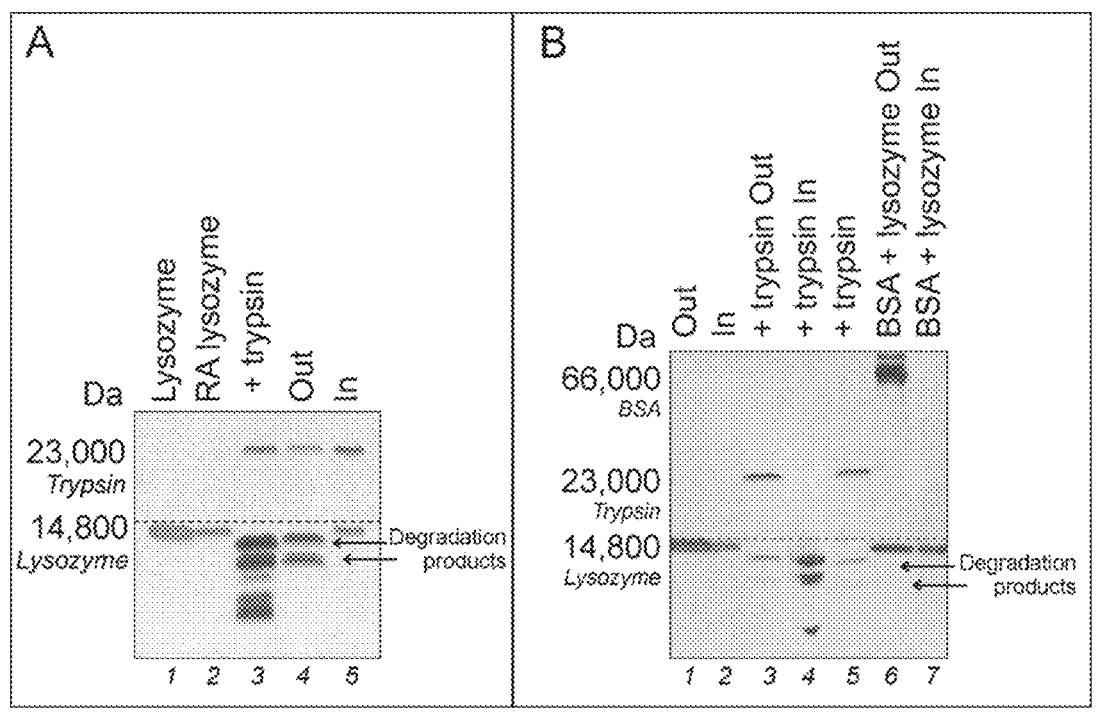
FIG. 15. SDS PAGE analysis of reduced and alkylated lysozyme exposed to tryptic digestion and incubated with particles+bait and –bait. (A) Reduced and alkylated lysozyme+trypsin incubated with NIPAm/AAc particles: Lane 1) lysozyme, 2) reduced and alkylated lysozyme, 3)+trypsin, 4) NIPAm/AAc supernatant (Out), 5) NIPAm/AAc particles (In). (B) Reduced and alkylated lysozyme incubated with NIPAm particles: lane 1) NIPAm particles supernatant (Out), 2) NIPAm particles (In), 3)+trypsin NIP Am supernatant (Out), 4)+trypsin NIPAm particles (In), 5)+trypsin, 6) BSA+reduced and alkylated protein solution incubated with NIP Am particles, supernatant (Out), 7) NIPAm particles (In).

Even if products of enzymatic degradation were clearly shown in the above presented results, the unfolded state of lysozyme is known to contain region resistant to trypsin proteolysis (Noda et a., *Biopolymers,* 1994, 34, (2), 217-226). Therefore, incubation with particles was repeated with reduced and alkylated lysozyme in order to exclude any bias. Lysozyme was reduced by incubation with Dithiothreitol (DTT) (10 mM) in NH4HC03 buffer (50 mM, pH 8) containing urea (2 M) for one hour at room temperature. Iodoacetamide was added to the solution to a final concentration of 50 mM and let react in the dark for 30 minutes. Buffer was exchanged and protein washed with MilliQ water by means of Centricon centrifugal filter units (Millipore) with MWCO of 3,000 Da. Lysozyme was resuspended in NH4HC03 (pH 8,100 mM) to an estimated final concentration of 0.5 mg/mL; trypsin (0.05 mg/mL) and NIPAm/AAc particles were added and the solution was incubated for 1 hour at 37° C. Particles were washed as previously described and loaded on SDS PAGE. In FIG. 15A it is shown that particles are able to protect lysozyme from degradation even in its reduced and alkylated form.

In order to better understand the mechanism of protection from proteolysis, an experiment was performed with plain particles. NIP Am particles were incubated at 37 C in a pH 7 NH4HC03 (100 mM) solution containing reduced and alkylated lysozyme (0.5 mg/mL) and trypsin (0.05 mg/mL) for one hour. The results are reported in FIG. 15B and show products of lysozyme degradation inside the particles. This suggests that the AAc bait plays a fundamental role in protecting proteins from degradation.

The development and application of hydrogel bait-containing particles as a new tool for harvesting and concentrating small molecule analytes and biomarker candidates from biological fluids has been described, allowing high throughput analysis of low-abundance and low molecular weight components. These nanoparticles present a rapid and straightforward workflow for direct utility in raw body fluids, while the work herein described the particles with a negative charge that preferentially bind cationic species, positively charged particles such as a NIPAm/allylamine copolymer could be used to selectively harvest and concentrate anionic species from biological fluids. Similarly, hydrophobic metabolites could be captured for comprehensive metabolomic studies by using more hydrophobic particles such as NIPAm/styrene copolymers. Analyte-specific chemical or protein or nucleic acid affinity baits can be incorporated. For example, boronate-containing particles, which are known to bind saccharides, would be utilized to sequester glycoproteins from solution (Ivanov et al., *Journal of molecular recognition* 2006, 19, (4), 322-31). Consequently, NIPAm-allylamine copolymers are currently being synthesized that contain a bait for anionic proteins. Moreover, p-vinylphenylboronic acid (VPBA) is under consideration as a copolymer for harvesting of sugars and nucleic acids. Further affinity baits such as triazinil-based reactive dyes (that have affinity towards proteins), hexadecylamine (for lipids uptake) and cyclodextrins (able to associate small molecules) are being noncovalently or covalently immobilized within the particles. In particular the bait chemistry described above has been used to harvest the following small metabolites L-Dopa, homogentisic acid, Dopamine, Dopac and 5-hydroxyindoleacetic acid. This extends the utility of the technology to the realm of metabolomics.

Combining a variety of affinity chemistries with a size-sieving tool in a one-step process could have enormous utility for disease marker discovery and analysis workflows.

In the workflow presented in this study, proteins are denatured when eluted out of particles and then analyzed in mass spectrometry for biomarker discovery. Nevertheless, it is important to note that the harvesting conditions are conducted with native protein mixtures. This permits future applications that require the analytes of interest to be in their native state (immulite, radioimmunoassays). For these applications it would important that proteins are not denatured when released from the particles. Ahmad and colleagues have demonstrated, using circular dichroism, that molecules for drug delivery released from NiPam particles by temperature changes retained their native conformational state (Ahmad et al., *Colloid & Polymer Science* 2002, 280, (4), 310-315). Consequently possible means of eluting native proteins from the particles include modifying the temperature or pH of the solution, increasing the ionic strength, or electro eluting the proteins under non denaturing conditions, in the absence of detergent.

Example 12

NIPAm/AAc Core—NIPAm Shell Particles Synthesis

In this particle architecture, a core, containing affinity bait moieties, is surrounded by a NIPAm shell. The sieving capability of the NIPAm shell will shield the core and its affinity bait groups from larger molecules that may be present and could compete with the intended low-abundance low molecular weight molecular targets for binding to the affinity bait in the core. A shell solution was prepared by dissolving NIPAm, 0.02 molar equivalents each of BIS and SDS in $H_2O$ and filtering the solution through a membrane filter. The solution was degassed under vacuum for several minutes and then purged with nitrogen for 2 h at room temperature with stirring. While the shell solution was purged, the core solution was prepared by dissolving NIPAm, 0.08 molar equivalents of AAc and 0.02 molar equivalents of BIS in H20 and then the solution was filtered. The core solution was then degassed and purged with nitrogen at 70° C. as described for the preparation of the NIP Am particles. Once the solution had equilibrated at 70° C. and stirred under nitrogen for 1 hour, APS (0.005 molar equivalents) was added to the core solution. After the NIPAm/AAc core reaction had been allowed to incubate for 3 h at 70° C. under nitrogen, the shell solution was added to the reaction flask followed by and additional aliquot of APS. The reaction was then allowed to stir at 70° C. under nitrogen for an additional 3 h. At which point, the reaction was removed from heat and allowed to stir overnight under nitrogen at room temperature. The particles were then collected and washed in the same fashion as described for the NIP Am particles.

Example 13

Core Shell Particles have the Same Molecular Sieving Cut Off as NIPAm/AAc

Figure 16:
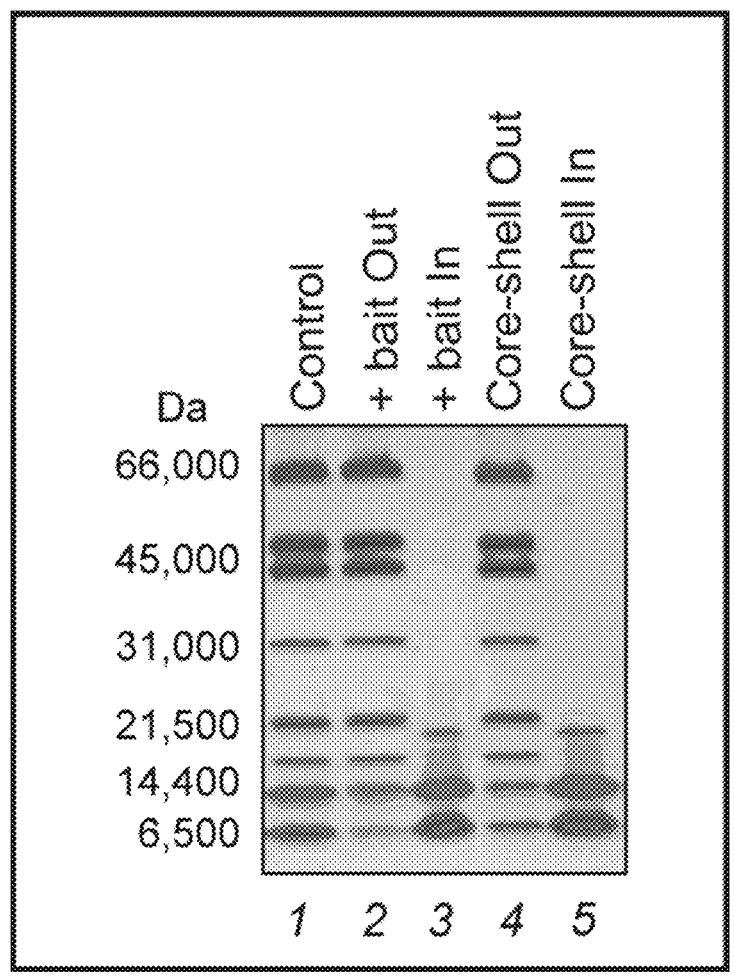
FIG. 16. Core shell particles have the same molecular weight sieving as NIPAm/AAc particles. Control protein solution was incubated with NIPAm/AAc and core shell particles. Lane 1) control protein solution, 2) NIPAm/AAc particles supernatant (Out), 3) NIPAm/AAc particles (In), 4) core shell particles supernatant (Out), 5) core shell particles (In).

Light scattering measurement of core shell particles diameter gave a value of 1048 nm for the NIPAm/AAc core and 1198 nm when the NIP Am shell was added. In order to determine if core shell particles had the same molecular weight cut off (MWCO) as NIPAm/AAc particles, a solution of protein molecular weight markers was used. The solution consisted of 0.5 mg/mL of each of the following proteins: aprotinin (MW 6,500 Da, Sigma-Aldrich), lysozyme (MW 14,400 Da, Sigma-Aldrich), trypsin inhibitor (MW 21,500 Da, Invitrogen), carbonic anhydrase (MW 31,000 Da, Sigma-Aldrich), ovalbumin (MW 45,000 Da, Sigma-Aldrich), and BSA (MW 66,000 Da, Fisher Scientific) dissolved in Tris (pH 7, 50 mM). Incubation time was 1 hour and particles were washed as described in the manuscript. SDS PAGE analysis reported in FIG. 16 shows a substantial agreement in MWCO values for the two types of particles.

Example 14

Core Shell Particles Protect Lysozyme from Chymotrypsin Enzymatic Degradation

Figure 17:
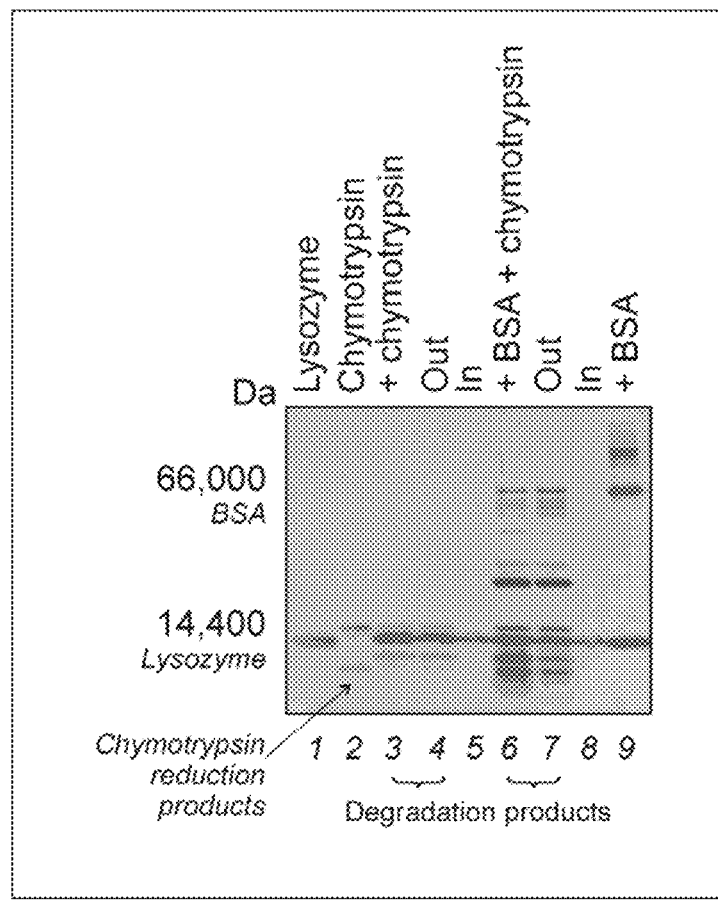
FIG. 17. Core shell particles protect lysozyme form chymotrypsin proteolysis. Lane 1) lysozyme, 2) chymotrypsin, 3) lysozyme+chymotrypsin, 4) lysozyme+chymotrypsin incubated with core shell particles, supernatant (Out), 5) lysozyme+chymotrypsin incubated with core shell particles, particles (In), 6) lysozyme+BSA+chymotrypsin, 7) lysozyme+BSA+chymotrypsin incubated with core shell particles, supernatant, 8) lysozyme+BSA+chymotrypsin incubated with core shell particles, particles (In), 9) lysozyme+BSA.

Another protease, α-chymotrypsin (MW 25,000 Da, pI=8.75, Sigma), was chosen to prove the ability of particles to protect proteins from degradation. α-chymotrypsin was used at a ratio of 1:10 (w/w) for α-chymotrypsin:lysozyme. Lysozyme digestion was performed in 100 mM Tris HCl containing 10 mM CaCl2, pH 7.8, at 30° C. for 3 hours. Core shell particles were incubated with lysozyme and trypsin in the digestion conditions described above. Also in this case, particles protected lysozyme from chymotrypsin degradation (FIG. 17, lane 5). Lysozyme degradation is also evident in the incubation without particles (FIG. 17, lane 3).

In relation to capturing particles in bodily fluid for such activities as "doping" detection, the following practical procedure and method is beneficial.

N-isopropylacrylamide (NIPAm) based particles that contain different flavors of baits to perform affinity capture of analytes in solution are available to target the following classes of molecules:

1. Cationic proteins & polypeptides (bait: acrylic acid)
2. Anionic proteins & polypeptides (bait: allylamine, 1-vinylmidazole, N, N dimethylaminopropymethacrylamidel)
3. Proteins & polipeptides in general (bait: Cibacron blue F3GA, Procion Red H8BN)
4. Small molecules, cholesterol (bait: cyclodextrin)
5. Polysaccharides, glycopeptides, RNA (bait: p-vinylphenyl Boronic Acid, NAcryoyl m-aminophenyl Boronic Acid)
6. Phosphopeptides (bait: Ti02)

This particles library has been tested in order to capture a mixture of acidic small proteins that mimicked hGH. The mixture contained the following proteins: Beta Caseine, 25 KDa, pI 4.98; S100A6 10 KDa, pI 5.32; Marcks 3.3 KDa, pI 4.2; Angiotensin 1, 1.3 KDa, pI 6.92 dissolved at the concentration of 1 uM in 50 mM Tris HCl pH 7.

Figure 18:
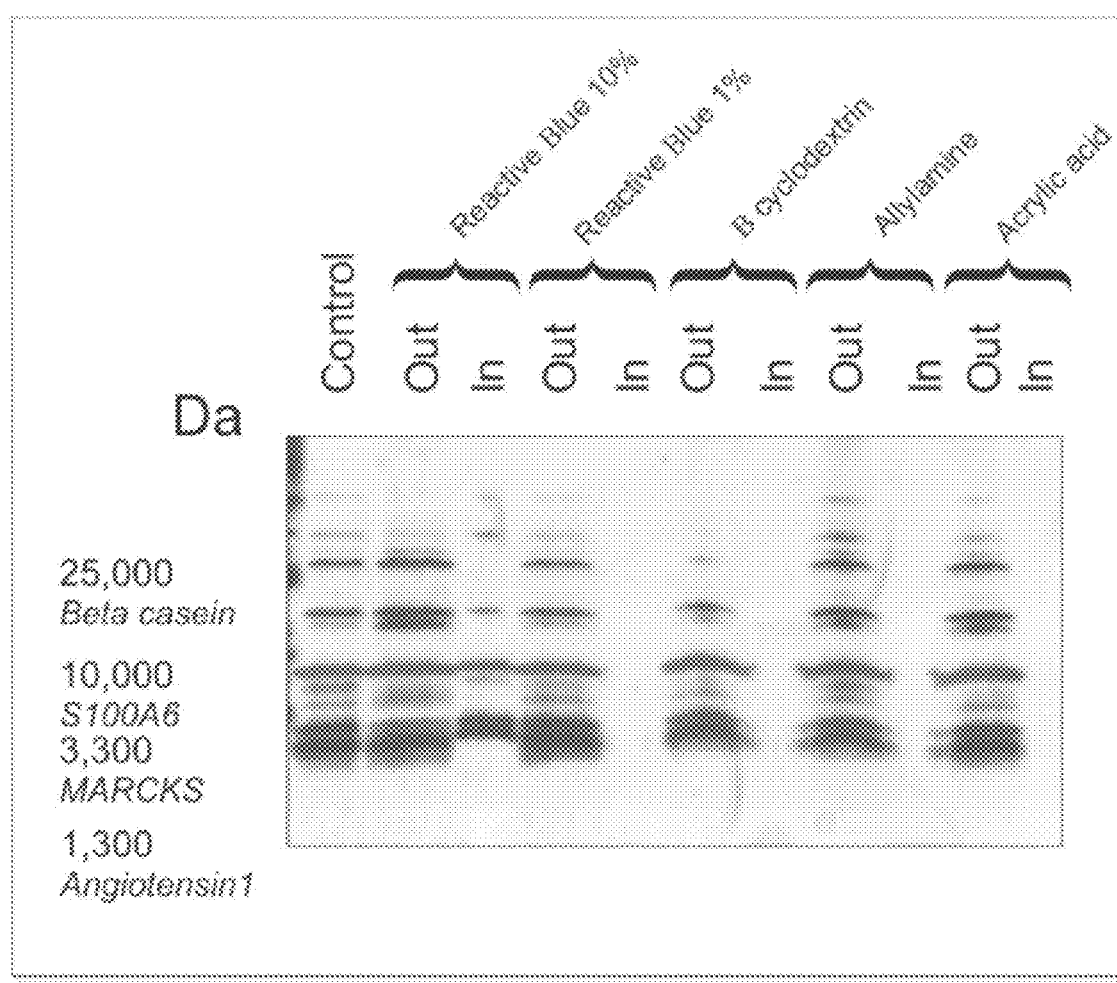
FIG. 18 shows results from SDS-PAGE analysis which showed that particles loaded with Cibacron Blue dye were the only batch of particles capable of harvesting proteins from solution.

SDS-PAGE analysis showed that particles loaded with Cibacron Blue dye were the only batch of particles capable of harvesting proteins from solution (FIG. 18). It should be noted that the reactive blue dye is the same and consequently also referred to as the Cibacron Blue.

The hydrogel nanoparticles were prepared via precipitation polymerization under a nitrogen atmosphere using a protocol based on that reported by Jones and Lyon for the synthesis of NIPAm-co-AAc particles (10).

N-Isopropyl acrylamide (NIPAm), N—N'-methylenebis (acrylamide) (BIS), potassium persulfate (KPS), allylamine (AA), and Reactive Blue 2 were purchased from Sigma-Aldrich. All reagents were used as received. Water for all reactions, solution preparation, and polymer washing was distilled, purified with a Millipore Milli-Q water purification system to a resistance of 18 MΩ and passed through a 0.2 μm filter.

Poly(NIP Am-co-AA) Nanoparticles (10% AA)

NIPAm (0.89 g, 7.83 mmol), BIS (0.042 g, 0.27 mmol) were dissolved in 30 mL of H20 and then filtered in the same manner as above. The solution was purged with nitrogen for 15 min at room temperature and medium stir rate before AA (0.051 g, 0.90 mmol) was added. The solution was purged with nitrogen for another 15 min and then heated to 75° C. The basis for this specific step in the polymerization method of the poly(NIPAm-co-AA) particle can be found elsewhere (11). KPS (0.0070 g, 0.025 mmol) in 1.0 mL of H20 was added to the solution to initiate polymerization. The reaction was maintained at 75° C. under nitrogen for 3 h. After 3 h, the reaction was allowed to cool to room temperature overnight. The particles were then harvested and washed via centrifugation (Eppendorf 5415R centrifuge) for 20 minutes at 23° C. and 16,100 ref. The supernatant was decanted and the particles were redispersed in 1.0 mL H20. This concentration/redispersion process was repeated for a total of five washes.

Poly(NIPAm-Co-AA) Nanoparticles (1% AA)

Particles containing 1% AA were generated using the method described above with minor adjustment. In synthesizing the 1% AA poly(NIPAm-co-AA) particles, NIP Am (0.97 g, 8.64 mmol) and AA (0.0067 g, 0.090 mmol) were used. The amount of BIS (0.042 g, 0.27 mmol) and KPS (0.0070 g, 0.025 mmol) used were unchanged.

Blue-Dye Poly(NIPAm-Co-AA) Nanoparticles (10% AA)

Reactive Blue 2 (0.38 g, 0.45 mmol) was dissolved in 5 mL of 0.1 M aqueous sodium carbonate. The poly(NIPAm-co-AA) solution (5 mL volume) was purged with nitrogen for 15 min at medium stir rate in a 100 mL three-neck round-bottom flask, after which solid sodium carbonate (0.053 g) was added. The solution was then allowed to stir at room temperature under nitrogen for ~1 min. The Reactive Blue 2 solution was then added, and the combined reaction mixture was then allowed to proceed at room temperature under nitrogen for 48 h. The particles were then harvested and washed via centrifugation (Eppendorf 5415R centrifuge) for 20 minutes at 23° C. and 16,100 ref. The supernatant was decanted and the particles were redispersed in 1.0 mL H20. This concentration/redispersion step was repeated until the supernatant was clear.

Dye Loading Determination

Dye loading was determined via spectrophotometry (Thermo Spectronic 20+). Different amounts of Reactive Blue 2 were dissolved in H20 to make stock solutions with concentrations ranging from 0.09 mM to 0.11 mM. A calibration curve was constructed using the stock solutions. Samples of the combined supernatant from the entire concentration/redispersion process were prepared by making 1:1125 dilution in H20. The absorbance of the supernatant was taken at wavelength 608 nm and the concentration was extrapolated from the calibration curve.

Recombinant human hGH (22 KDa, pI 5.27—Humatrope, Lilly) was diluted in 50 mM Tris HCl pH 7, 0.01 mg/ml and incubated with 100 ul of particles loaded with different amount of Blue Dye (1% and 10%). After one hour incubation samples were centrifuged for 7 min. at 16.1 ref, 25 degrees C., to separate particles from the supernatant. Beads were resuspended in 1 ml of water and centrifuged. Washing and centrifugation steps were repeated 3 times.

Figure 19:
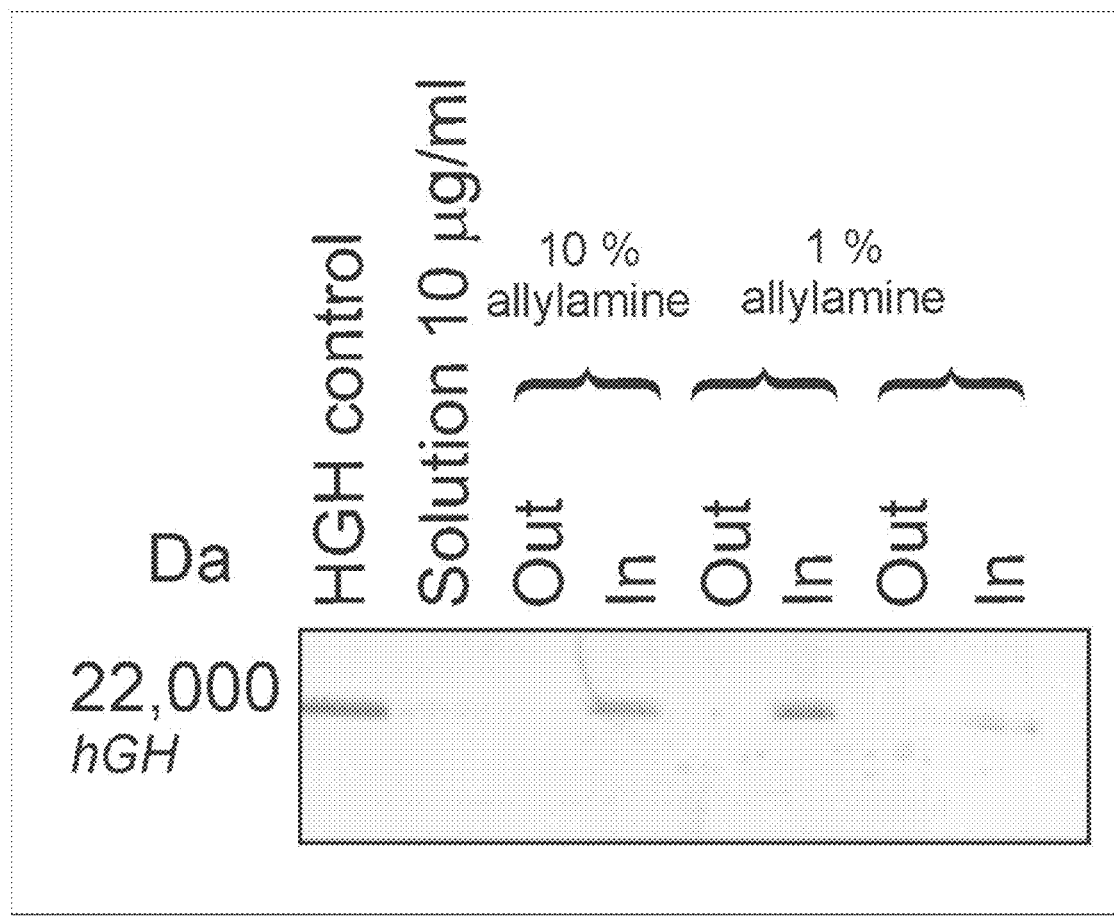
FIG. 19. displays results of SDS PAGE analysis which showed that particles captured hGH in solution and that the uptake was dependent on the percentage of loaded dye FIG. 20a and FIG. 20b. Showing bands where, in the optimal conditions, particles were capable to raise hGH concentration from a not detectable level (lane 2) to a clearly visible band (lane 4, 6, 8, 18, 20).

SDS PAGE analysis showed that particles captured hGH in solution and that the uptake was dependent on the percentage of loaded dye (FIG. 19).

In order to recreate conditions similar to physiologic urine, we studied the effect of Urea, salts and different pH values on the particles behavior.

Solutions of 0.01 mg/ml hGH in the following buffers: Urea 0.7 mg/ml, KCl 6.0 mg/ml, 50 mM Sodium Citrate Buffer pH 4, 5 and 6, 50 mM Tris HCl pH 7 and 8, 50 mM Carbonate-Bicarbonate Buffer pH 10 were incubated with 100 ul of particles for one hour. We centrifuged and washed the particles as described above. SDS PAGE analysis demonstrated that physiological concentrations of Urea and salts did not hinder hGH uptake by particles and the optimal pH range is 4 to 6, while higher pH levels showed lower to no uptake.

Figure 20A:
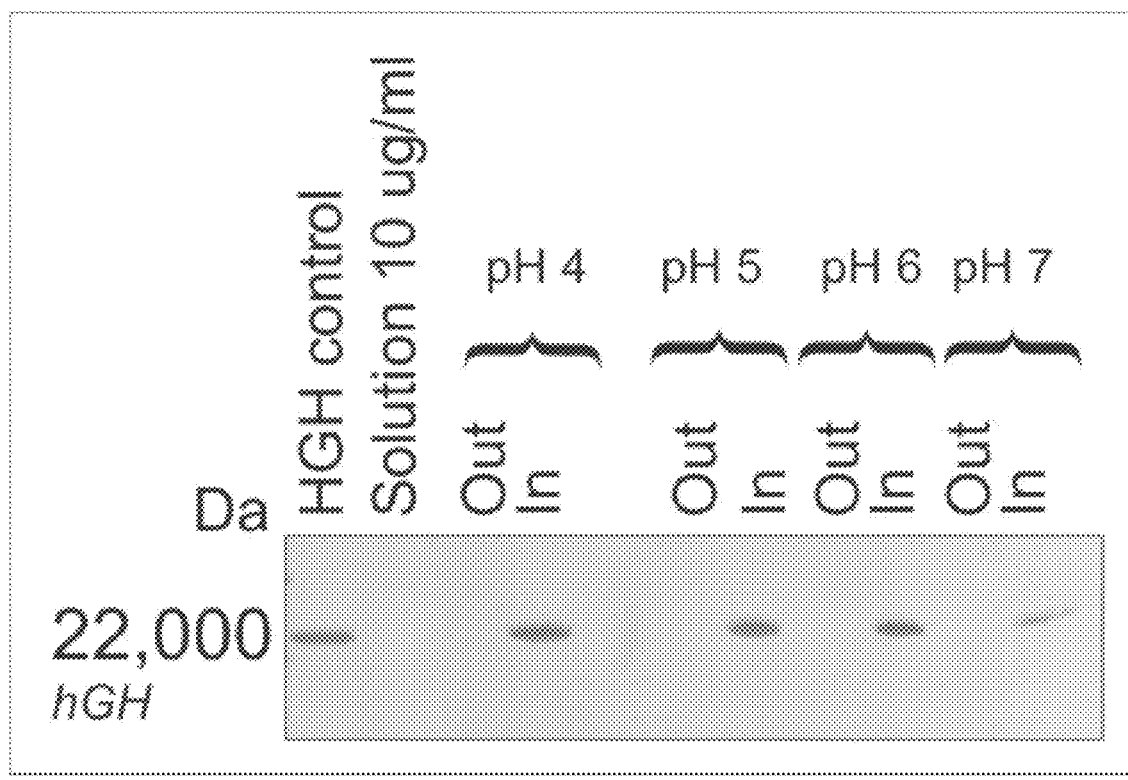
Figure 20B:
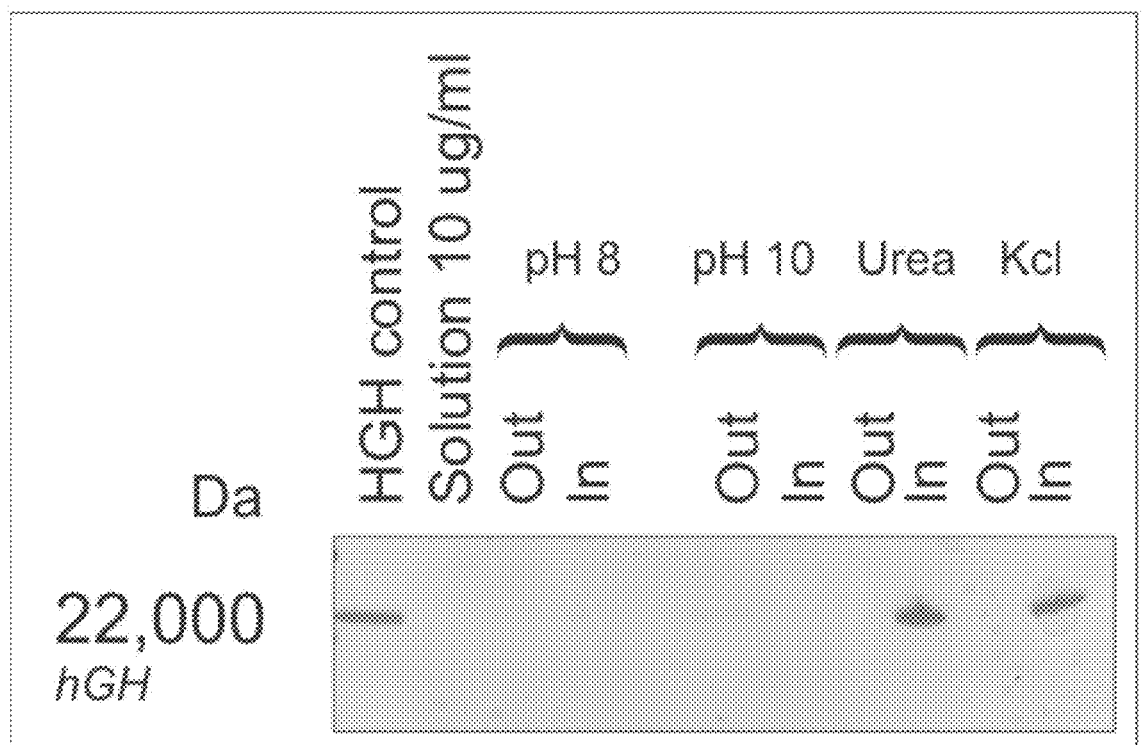
Figure 21:
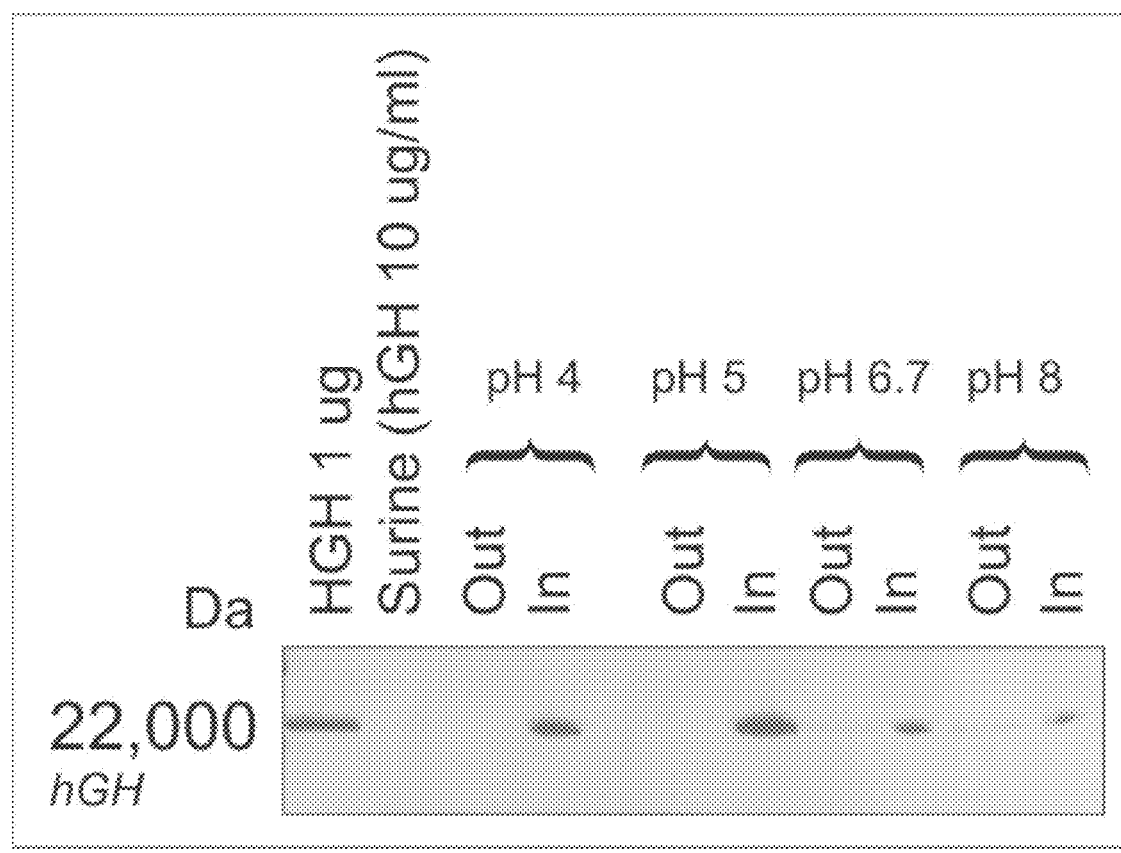
FIG. 21 shows the same experiment as FIG. 20a and FIG. 20b, but with varied pH levels (4, 5, 6.7, 8) with synthetic urine (SURINE, Dyna-Tek Industries) which is routinely used as negative control for different urine tests, obtaining sequestration of hGH at each pH point and assessing pH 5 as the optimal uptake condition.

In the optimal conditions, particles were capable to raise hGH concentration from a not detectable level (lane 2) to a clearly visible band (lane 4, 6, 8, 18, 20) (FIG. 20a-20b). As shown in FIG. 21 We performed the same experiment varying pH levels (4, 5, 6.7, 8) with synthetic urine (SURINE, Dyna-Tek Industries) which is routinely used as negative control for different urine tests, obtaining sequestration of hGH at each pH point and assessing pH 5 as the optimal uptake condition.

Relying upon the aforementioned results, we decided to carry out the incubations at pH 5 and then to increase the pH in order to elute hGH from particles.

Figure 22:
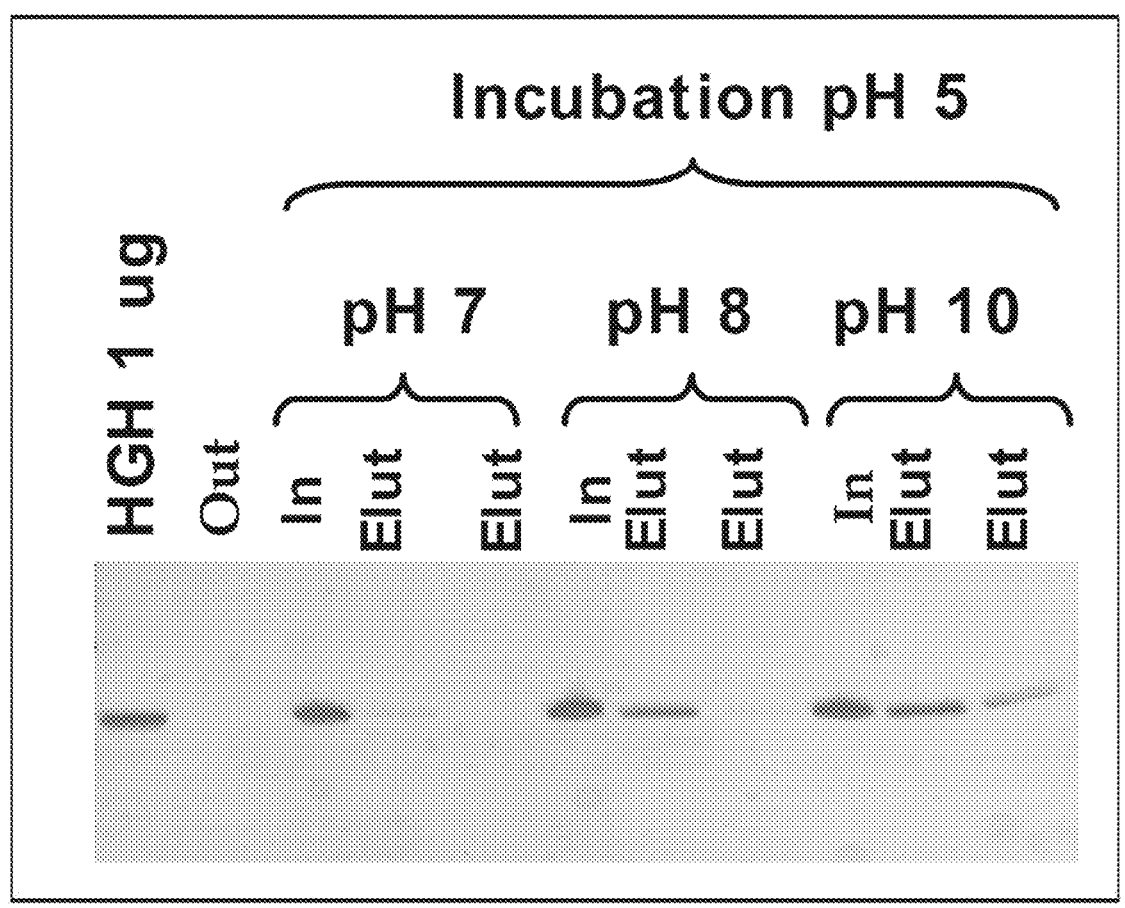
FIG. 22 showing partial elution at all PH, with higher yield at more basic conditions.

Aliquots of 1 ml of 0.01 mg/ml hGH in synthetic urine at pH 5 were incubated with 100 ul of dye particles and washed as previously described. The following elution buffers were tested: 50 mM tris HCl pH 7 and 8, 50 mM Carbonate-Bicarbonate Buffer pH 10. The previously washed pellets were resuspended in the elution buffers and incubated for 15 min. and centrifuged (7 min, 25 C, 16.1 rcf). The elution step was repeated 2 times. We obtained partial elution at all pH, with higher yield at more basic conditions (FIG. 22).

Aiming at complete retrieval of hGH from dye particles, we tested stronger elution buffers, namely Acetonitrile 50%/NH4C03 50 mM and Acetonitrile 60%/NH40H 4%, and relying on the property of particles to shrink at higher temperature, we performed the elution at 38 C for one hour.

Figure 23:
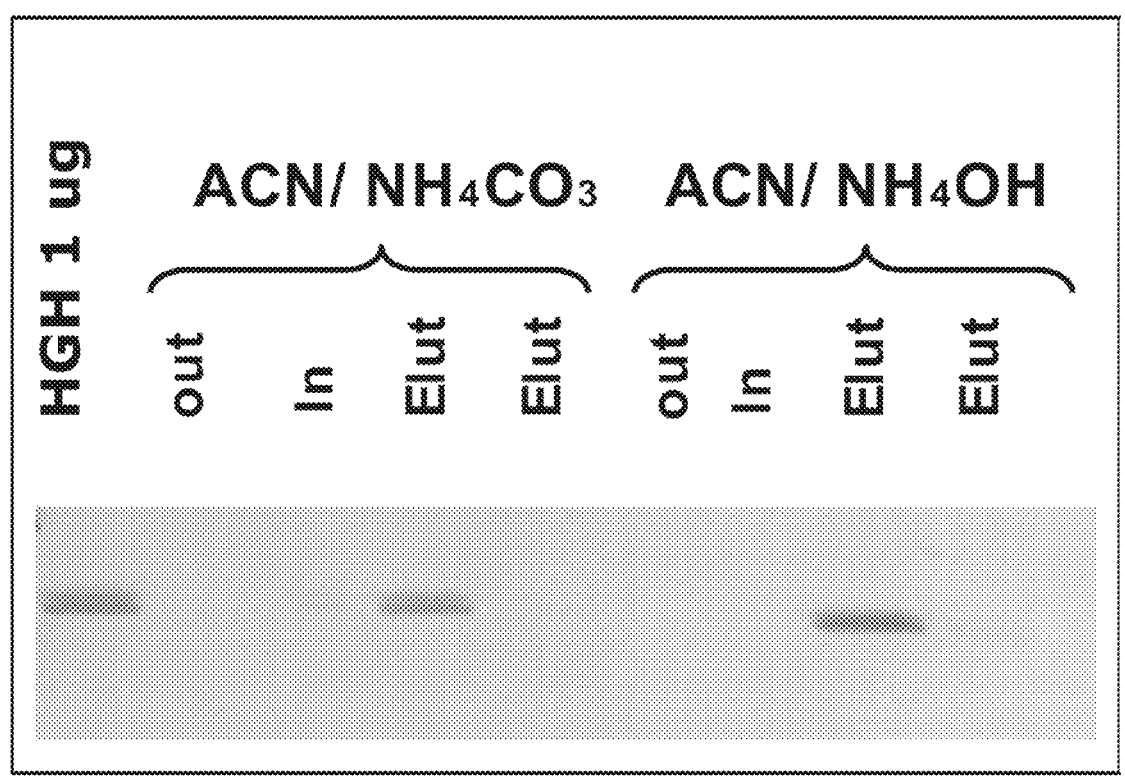
FIG. 23 displays that entire elution was obtained by using Acetonitrile 60%/NH40H 4% buffer and almost entire elution was obtained with Acetonitrile 50%/NH4C03 50 mM

Entire elution was obtained by using Acetonitrile 60%/NH40H 4% buffer and almost entire elution was obtained with Acetonitrile 50%/NH4C03 50 mM (FIG. 23).

We performed a time course to test the stability of the uptaken hGH over a period of 48 hours. Dye particles (100 ul) were incubated with 1 ml of 0.01 mg/ml hGH in synthetic urine for 1, 4, 24, and 48 hours at room temperature. SDS PAGE analysis showed no detectable loss of hGH in each incubation time.

In order to obtain a quantitative measurement of hGH in our samples, after concentration from urine by nanoparticles, we applied an immunometric assay (IMMULITE-Siemens Medical Solution Diagnostic), routinely used in clinical setting for serum measurements. Immulite detection limits span between 40 ng/ml and 0.05 ng/ml.

Estimated hGH concentration in healthy individual's urine is in the range of pg/ml, and therefore below the detection limit of Immulite.

Figure 24:
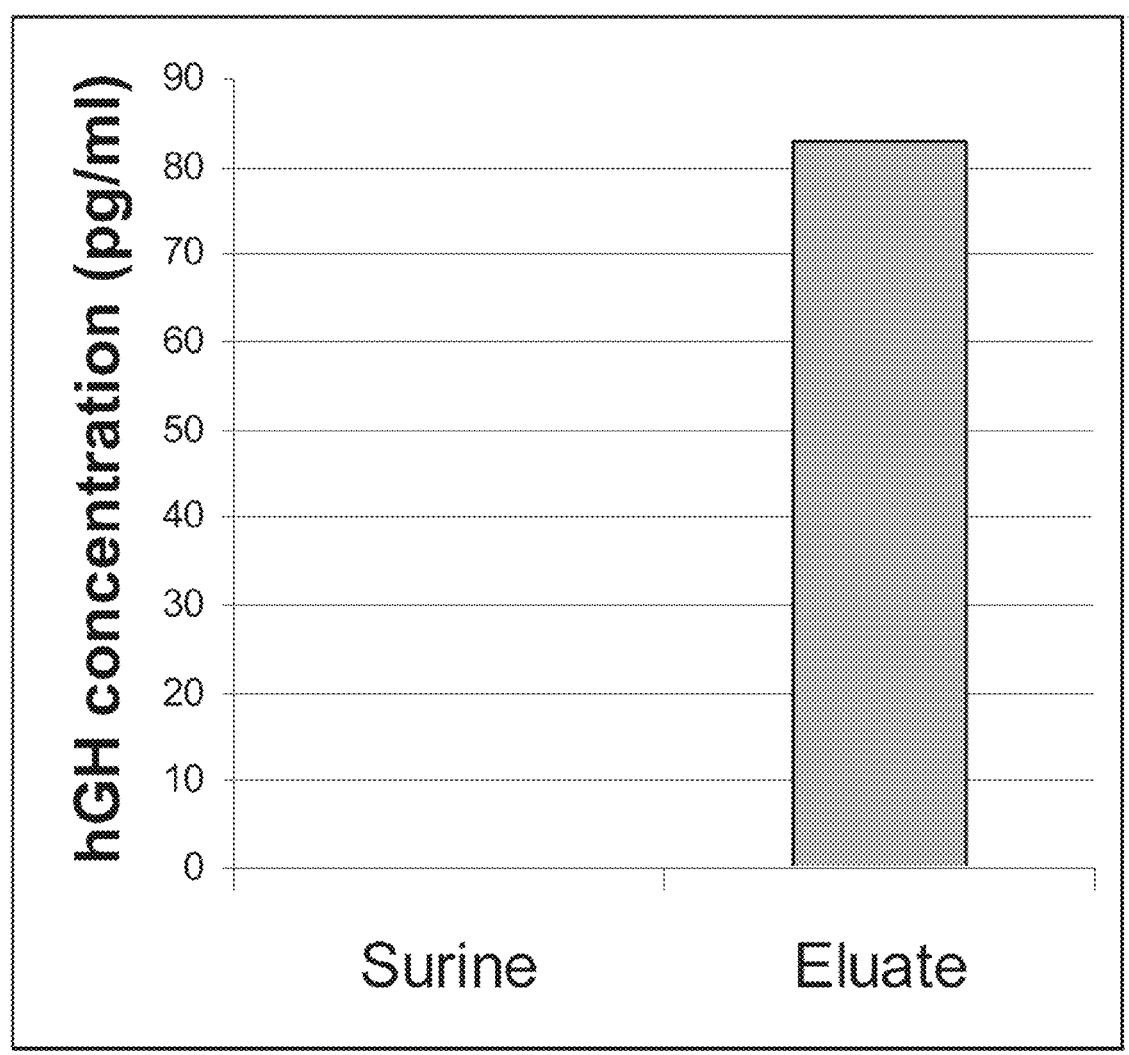
FIG. 24 shows that previously undetectable levels of hGH were recovered from the particles and successfully quantified by Immulite at the concentration of 83 pg/ml.

Aliquots of 1 ml of hGH solution in synthetic urine below the detection limit of Immulite (0.05 ng/ml) were incubated for 1 hour with 100 ul of dye particles, protein were eluted from the washed particles with Acetonitrile 60%/NH40H 4% buffer at 38 C in a total volume of 30 ul. Immulite readings were performed on a volume of 30 ul. As shown in FIG. 24 previously undetectable levels of hGH was recovered from the particles and successfully quantified by Immulite at the concentration of 83 pg/ml. A similar experiment with a more concentrated hGH solution was performed. The concentration of hGH in the stating solution was 0.138 ng/ml, whereas the concentration of hGH recovered from particles was 1.90 ng/ml yielding a concentration factor of about 14 fold.

CONCLUSIONS

The experiments here reported demonstrated that

Cibacron blue bait loaded hydrogel particles harvest and concentrate hGH from model solutions and synthetic urine at pH<7 in the presence of physiologic salt and urea concentrations The harvested hGH is stable for at least 48 hours hGH was successfully eluted by means of strong bases (NH40HINH4HC03-acetonitrile)

The elution method was totally compatible with immunometric clinical immunoassay measurement (Immulite)

Undetectable concentrations of hGH (below 0.05 ng/ml) in a standard detection volume of 30 uL could be increased ten fold to reach a fully detectable concentration (sample volume 1 mL)

The present invention includes a method for producing capturing particles in bodily fluid. This method is comprised of mixing N-isopropylacrylamide (NIPAm) based particles that contain a type of bait in a solution and performing affinity capture of analytes, the analytes contained in the solution. The bait is acrylic acid when cationic proteins and polypeptides are in the solution. The bait also is allylamine, I-vinylmidazole, and N, N' dimethylaminopropymethacrylamidel when anionic proteins and polypeptides are in the solution or the bait is cibacron blue F3GA and procion red H8BN when proteins & polipeptides are in the solution. It also should be noted that the bait is p-vinylphenyl boronic acid and N-Acryoyl m-aminophenyl boronic acid when polysaccharides, glycopeptides, and RNA are in the solution wherein the bait is TiO2 when phosphopeptides are in the solution.

Moreover, the present invention is a capture particle for isolating an analyte from a mixture, comprising of a polymeric matrix, with the polymeric matrix having a pore size that under certain conditions allows for the analyte to enter the polymeric matrix while excluding other compounds from the mixture from entering the polymeric matrix. the analyte is selected from the group consisting of: metabolites, proteins, RNA, micro RNA, DNA, glycoproteins, lipids, glycolipids, proteolipids, hormones, cytokines, growth factors, biomarkers, drug compounds, synthetic organic compounds, volatile odorants, toxicants and pollutants. The polymeric matrix is expandable and contractible and when the polymeric matrix expands or contracts, the pore size of the gel matrix expands or contracts, respectively. The polymeric matrix is expandable and contractible in response to an applied stimulus and the applied stimulus is a thermal, electrical, magnetic, ultrasound, pressure, radiant, laser, osmotic, or pH change. The polymeric matrix is expandable or contractible upon treatment with an enzyme. The present invention also has an attractant. The attractant is sequestered with the capture particle and covalently bonded to the capture particle. The attractant also is integrated into the polymeric matrix and is an affinity ligand. The affinity ligand comprises an antibody or protein, an aptamer, nucleic acid, a drug, a chemical, a metabolite, a lipid, a glycolipid, a phospholipid, a polypeptide, an affinity group, or a metal group and is further comprised of a detectable label. The attractant is acrylic acid when cationic proteins and polypeptides are in the mixture, with the attractant being allylamine, I-vinylmidazole, and N, N' dimethylaminopropymethacrylamidel when anionic proteins and polypeptides are in the mixture. The attractant is cibacron blue F3GA and procion red H8BN when proteins & polipeptides are in the mixture and the attractant is cyclodextrin when cholesterol is in the mixture. The attractant is p-vinylphenyl boronic acid and N-Acryoyl m-aminophenyl boronic acid when polysaccharides, glycopeptides, and RNA are in the mixture and the attractant is TiO2 when phosphopeptides are in the mixture.

The present invention also relates to a capture particle for isolating an analyte from a mixture. This is comprised of a co-polymeric matrix comprising a structural monomer and an affinity monomer, with the polymeric matrix having a pore size that under certain conditions allows for the analyte to enter the polymeric matrix while excluding other compounds from the mixture from entering the polymeric matrix and where the analyte is selected from the group consisting of: metabolites, proteins, RNA, micro RNA, DNA, glycoproteins, lipids, glycolipids, proteolipids, hormones, cytokines, growth factors, biomarkers, drug compounds, synthetic organic compounds, volatile odorants, toxicants and pollutants. The capture particle has a molecular weight cutoff size of about 5 to about 100 kDa. The capture particle also can have a molecular weight cutoff size of about 20 to about 50 kDa. The structural monomer is selected from the group consisting of: acrylamide and derivatives thereof, N-alkyl substituted acrylamides; N,N-methylenebisacrylamide, N,N-cystaminebisacrylamide, N-vinylalkylamides, acrylic acid, methacrylic acid, allylamine, styrene, benzyl glutamate, 2-ethylacrylic acid, 4-vinylpyridine, silicone, hydroxyethyl methacrylate, ethylene oxide, butylenes terephthalate, 2-acrylamido-2-methyl-1-propanesulfonic acid, vinylpyrrolidone, ethylenevinyl acetate, lactide, glycolide, caprolactone, hydroxyalkanoate, chitosan, hyaluronic acid, starch, cellulose and agarose. The structural monomer is N-isopropylacrylic acid. Meanwhile, the affinity monomer comprises a positively charged moiety and the positively charged moiety is selected from the group consisting of: amine groups and amide groups. The affinity monomer comprises a negatively charged moiety, where the negatively charged moiety is selected from the group consisting of: carboxylic acid groups, hydroxyl groups, thiol groups and phosphate groups.

While the affinity monomer is selected from the group consisting of: affinity dyes, boronic acid groups, nucleic acids, glycopeptides, glycoproteins, cyclodextrins, calixarenes, porphyrin groups, and aliphatic groups, the affinity monomer is acrylic acid, particularly in regard to when cationic proteins and polypeptides are in the mixture. The affinity monomer is allylamine, I-vinylmidazole, and N, N' dimethylaminopropymethacrylamidel when anionic proteins and polypeptides are in the mixture. The affinity monomer is cibacron blue F3GA and procion red H8BN when proteins & polipeptides are in the mixture and the affinity monomer is cyclodextrin when cholesterol is in the mixture. Also, the affinity monomer is p-vinylphenyl boronic acid and N-Acryoyl m-aminophenyl boronic acid when polysaccharides, glycopeptides, and RNA are in the mixture and the affinity monomer is TiO2 when phosphopeptides are in the mixture. In addition, the captured analyte is eluted by appropriate buffers and by electro-elution.

A kit for capturing particles in bodily fluid also is envisioned with the present invention to include a collection vile, a compartment in the collection vile and particles in the compartment.

The kit also is comprised of bodily fluid in the collection vile, with the compartment being loose and porous.

We claim:

1. A method of capturing analytes in a bodily fluid, comprising:
    mixing a solution containing open-meshwork hydrogel capture particles that contain an analyte binding affinity molecule with a fluid solution that contains an analyte of interest;
    further comprising the analyte binding affinity molecule capturing the analyte of interest against a concentration gradient resulting in a higher analyte of interest concentration within the volume of the open-meshwork hydrogel capture particles; and
    further comprising eluting the analyte of interest, once captured, by a chemical treatment that dissociates the analyte of interest from the analyte binding affinity molecule within the volume of the open-meshwork hydrogel particles such that the pore size of the open-meshwork hydrogel capture particles does not change.

* * * * *